United States Patent [19]

Labrie et al.

[11] Patent Number: 5,434,146
[45] Date of Patent: * Jul. 18, 1995

[54] CONTROLLED RELEASE SYSTEMS AND LOW DOSE ANDROGENS

[75] Inventors: Fernand Labrie; Martin Lepage, both of Quebec, Canada

[73] Assignee: Endorecherche, Inc., Quebec, Canada

[*] Notice: The portion of the term of this patent subsequent to Nov. 8, 2011 has been disclaimed.

[21] Appl. No.: 900,817

[22] Filed: Jun. 24, 1992

Related U.S. Application Data

[63] Continuation-in-part of Ser. No. 724,532, Jun. 28, 1991, abandoned.

[51] Int. Cl.⁶ .............................................. A61K 31/56
[52] U.S. Cl. ................................. 514/169; 514/170; 514/177; 514/179; 523/113; 424/422
[58] Field of Search ............... 514/169, 170, 177, 179; 523/113; 424/422

[56] References Cited

U.S. PATENT DOCUMENTS

| | | | |
|---|---|---|---|
| 3,773,919 | 11/1973 | Boswell . | |
| 4,107,071 | 8/1978 | Bayless | 252/316 |
| 4,166,800 | 9/1979 | Fong | 252/316 |
| 4,659,695 | 4/1987 | Labrie | 514/15 |
| 4,818,542 | 4/1989 | DeLuca | 424/491 |

(List continued on next page.)

FOREIGN PATENT DOCUMENTS

| | | |
|---|---|---|
| 0058481 | 8/1982 | European Pat. Off. . |
| 2010115 | 3/1970 | Germany . |
| 2051580 | 10/1970 | Germany . |
| 3503679 | 2/1985 | Germany . |
| 4036425 | 5/1991 | Germany . |

(List continued on next page.)

OTHER PUBLICATIONS

The Merck Index, 1989, Citation No. 7486, Pizotyline, p. 1194.

Chemical Abstracts, vol. 97, No. 4, 26 Jul. 1982, Columbus Ohio, Abstract No. 28542e.

The Merck Index, 1989, Merck & Co. Inc., Rahway, N.J., p. 909, No. 5677; p. 910 No. 5687.

Adair, F. E. (1947) The use of the male sex hormone in women with breast cancer, Surg. Gynecol. Obstet. 84:719–722.

Adair, F. E., Herrmann, J. B. (1946) The use of testosterone propionate in the treatment of advanced carcinoma of the breast. Ann. Surg 123:1023–1035.

Adair, F. E., Mellors, R. C., Farrow, J. H., Woodard, H. Q., Escher, C. S., Urban, J. A. (1949) The use of estrogens and androgens in advanced mammary cancer. J. Am. Med. Ass. 15:1193–1200.

Allegra, J. C., Lippman, M. E., Thompson, E. B., Simon, R., Barlock, A., Green, L., Huff, K. K., Do, H. M. T., Aitken, S. C. (1979) Distribution, frequency, and quantitative analysis of estrogen, progesterone, androgen, and glucocorticoid receptors in human breast cancer. Cancer Res. 39:1447–1454.

Aloia, J. F., Vaswanim, A. N., Yed, J. K., Ross, P., Ellis, K., Cohn, S. H. (1983) Determinants of bone mass in postmenopausal women. Arch. Int. Med. 143:1700–1704.

Anderson, L. C., Wise, D. L., Howes, J. F. (1976) An injectable sustained release fertility control system. Contraception 13:375–384.

(List continued on next page.)

Primary Examiner—Nathan M. Nutter
Attorney, Agent, or Firm—Ostrolenk, Faber, Gerb & Soffen

[57] ABSTRACT

Methods of treatment and prevention of estrogen-related diseases, and of fertility control, include low dose (e.g. less than 50 nanomolar serum concentration) administration of certain anabolic steroids, progestins and other substantially non-masculinizing androgenic compounds. Sustained release formulations substantially free of organic solvent, and sustained release formulations for maintaining low serum levels of androgen are disclosed.

16 Claims, 9 Drawing Sheets

U.S. PATENT DOCUMENTS

| | | |
|---|---|---|
| 4,826,831 | 5/1989 | Plunkett et al. ............... 514/170 |
| 4,987,268 | 1/1991 | Rauleder ....................... 568/616 |
| 5,043,331 | 8/1992 | Hirvonen et al. ................ 514/170 |

FOREIGN PATENT DOCUMENTS

| | | |
|---|---|---|
| 141652 | 12/1967 | New Zealand . |
| 145613 | 12/1969 | New Zealand . |
| 180683 | 10/1977 | New Zealand . |
| 180684 | 3/1978 | New Zealand . |
| 222761 | 10/1989 | New Zealand . |
| 2239798 | 7/1991 | United Kingdom . |

(List continued on next page.)

OTHER PUBLICATIONS

Baker, R. (1987) Controlled release of biologically active agents. John Wiley & Sons, Inc.

Beck, L. R., Tice, T. R. (1983) Poly(lactic acid) and poly(lactic acid-co-glycolic acid) contraceptive delivery systems. In: Advances in Human Fertility and Reproductive Endocrinology. Edited by D. R. Mishell Jr., vol. 2, Raven Press, New York, pp. 175–199.

Blossey, H. C., Wander, H. E., Kiebberling, J., Nagel, G. A. (1984) Pharmacokinetic and pharmacodynamic basis for the treatment of metastatic breast cancer with high-dose medroxyprogesterone acetate. Cancer 54:1207–1215.

Blumenschein, G. R. (1983) The role of progestins in the treatment of breast cancer. Semin. Oncol. 10:7–10.

Centola, G. M. (1985) Inhibition of endometrial carcinoma cell cultures by a synthetic androgen. Cancer Res. 45:6264–6267.

Colvard, D. S., Eriksen, E. F., Keeting, P. E., Wilson, E. M., Lubahn D. B., French, F. S., Riggs, B. L., Spelsberg, T. C. (1989) Identification of androgen receptors in normal human osteoblast-like cells. Proc. Natl. Acad. Sci. 86:854–857.

Deutsch, S., Benjamin, F., Seltzer, V., Tafreshi, M., Kocheril, G., Frank, A. (1987) The correlation of serum estrogens and androgens with bone density in the late postmenopause. Int. J. Gynecol. Obstet. 25:217–222.

Ehrlich, C. E., Young, P. C. M., Stehman, F. B., Sutton, G. P., Alfort, W. M. (1988) Steroid receptors and clinical outcome in patients with adenocarcinoma of the endometrium. Am. J. Obstet. Gynecol. 158:797–807.

Eriksen, E. F., Colvard, D. S., Berg, N. J., Graham, M. L., Mann, K. G., Spelsbert, C., Riggs, B. L. (1988) Evidence of estrogen receptors in normal human osterblast-like cells. Science 241:84–86.

Finkelstein, J. S., Linbanski, A., Neer, R. M., Greenspan, S. L., Rosenthal, D. I., Crowley, W. F. Jr (1987) Osteoporosis in men with idiopathic hypogonadotropic hypogonadism. Ann. Intern. Med. 106:354–361.

Gresser, J. D., Wise, D. L., Beck, L. R., Howes, J. F. (1978) Larger animal testing of an injectable sustained release fertility control system. Contraception 17:253–267.

Hall PE (1987) Long acting injectable preparations. Edited by E. Diczfalusy, M. Bydeman M. In:Fertility Regulation, Today and Tomorrow. New York, Raven Press, pp. 119–141.

Haller, F. G., Glick, J. H. (1986) Progestational agents in advanced breast cancer: an overview. Semin. Oncol. 13:2–8.

Hamblen EC (1957) Androgenic therapy for woman. South Med J 50: 743–750.

Hollo, I., Feher, T., Szucs, J. (1970) Serum dehydroepiandrosterone, androsterone and cortisol level in primary postmenopausal and other type osteoporosis. Acta Med. Hung. 27:155–160.

Hollo, I. Fehér, T. (1964) Studies on postmenopausal osteoporosis. I. Urinary excretion of 17-ketosteroid fractions in postmenopausal osteoporosis. Acta Med. Hung. 20:233–247.

Hollo, I., Szalay, F., Szucs, J., Boross, M. (1976) Osteoporosis and androgens. Lancet 1357.

Hortobagyi, G. N., Buzdar, A. M., Frye, D., Yap, H. Y., Hug, V., Pinnamaneni, K., Fraschini, G., Halvorson, H. C., Blumenschein, G. R. (1985) Oral medroxyprogesterone acetate in the treatent of metastatic breast cancer. Breast Cancer Res. Treatm. 5:321–326.

Horwitz, K. B. (1987) The structure and function of progesterone receptors in breast cancer. J. Steroid Biochem. 27:447–457.

Horwitz, K. B., Zava, D. T., Thilagar, A. K., Jensen, E. M., McGuire, W. L. (1978) Sterod receptor analyses of nine human breast cancer cell lines. Cancer Res. 38:2434–2439.

Jänne, O. A., Bardin, C. W. (1984) Steroid receptors and hormone action: physiological and synthetic andro- (List continued on next page.)

FOREIGN PATENT DOCUMENTS

| | | |
|---|---|---|
| 86/0110 | 2/1986 | WIPO . |
| WO8807816 | 10/1988 | WIPO . |
| 8903678 | 5/1989 | WIPO . |
| 90/10462 | 9/1990 | WIPO . |
| 9010462 | 9/1990 | WIPO . |

OTHER PUBLICATIONS gens and progestins can mediate inappropriate biological effects. Pharmacol. Rev. 36:35S–42S.

Kitchell, J. D. and Wise, D. L. (1985). [32]poly(lactic/-glycolic acid) biodegradable drug–polymer matrix system. In Methods in Enzumology, Academic Press, vol. 112, pp. 436–448.

Komm, B. S., Terpening, C. M., Benz, D. J., Graeme, K. A., Gallegos, A., Korc, M., Greene, G. L., O'Malley, B. W., Haussler, M. R. (1988) Estrogen binding, receptor mRNA, and biologic response in osteoblast–like ostersarcoma cells. Science 241:81–84.

Kramer, C. Y. (1956) Extension of multiple range tests to group means with unequal numbers of replications. Biometrics 12:307–310.

Labrie, C., Cusan, L., Plante, M., Lapointe, S., Labrie, F. (1987) Analysis of the androgenic activity of synthetic "progestins" currently used for the treatment of prostate cancer. J. Steroid Biochem. 28:379–384.

Labrie, C., Simard, J., Zhao, H. F., Pelletier, G., Labrie, F. (1990) Synthetic progestins stimulate prostatic binding protein messenger RNAs in the rat ventral prostate. Mol. Cell. Endocrinol. 68:169–179.

Labrie, F., Ferland, L., Lagacé, L., Drouin, J., Asselin, J., Azadian–Boulanger, G., Raynaud, J. P. (1977) High inhibitory activity of R5020, a pure progestin, at the hypothalamic–adenohypophyseal level on gonadotropin secretion. Fertil. Steril. 28: 1104–1112.

Larrea, F., Vilchis, F., Chavez B., Pérez, A. E., Garza–Flores, J., Pérez–Palacios, G. (1987) The metabolism of 19–nor contraceptive progestins modulates their biological activity at the neuroendocrine level. J. Steoid Biochem. 27:657–663.

Lea, O. A., Kvinnsland, S., Thorsen, T. (1989) Improved measurement of androgen receptors in human breast cancer. Cancer Res. 49:7162–7167.

Lim F. (1984) Biomedical Application of microencapsulation. Edited by F. Lim. CRC Press, BocaRaton.

Lippman, M. E. (1983) Antiestrogen therapy of breast cancer. Semin. Oncol. 10:11–19.

Lippman, M., Bolan, G., Huff, K. (1976) The effects of androgens and antiandrogens on hormone–responsive human breast cancer in long–term tissue cultur. Cancer Res. 36:4610–4618.

MacLaughlin, D. T., Richardson, G. S. (1979) Specificity of medroxyprogesterone acetate binding in human endometrium: interaction with testosterone and progesterone binding sites. J. Steroid Biochem. 10:371–377.

Mattson, W. (1983) Current status of high dose progestin treatment in advanced breast cancer. Breast Cancer Res. Treatm. 3:231–235.

Muechler, E. K., Kohler, D. (1988) Dihydrotestosterone–binding by human endometrium. Society for Gynecol. Invest. 8:104 (abst.).

Nathanson, I. T. (1947) Endocrine aspects of human cancer. Rec. Prog. Horm. Res. 1:261–291.

Need, A. G., Horowitz, M., Moris, H. A., Walker, C. J., Nordin, B. E. C. (1987) Effects of nadrolone therapy on forearm bone mineral contant in osteoporosis. Clin. Orthop. 225:273.

Nordin, B. E. C., Robertson, A., Seamark, R. F., Bridges, A., Philcox, J. C., Need, A. G., Horowitz, M., Morris, H. A., Deam, S. (1985) The relation between calcium absorption, serum dehydroepiandrosterone, and vertebral mineral density in postmenopausal women. J. Clin. Endocr. Metab. 60:651.

Ojasso, T., Delettré, J., Mornon, J. P., Turpin–VanDycke, C., Raynaud, J. P. (1987) Towards the mapping of the progesterone and androgen receptors. J. Steroid Biochem. 27:255–269.

Perez–Palacios, G., Chavez, B., Escobar, N., Vilchis, F., Lerrea, F., Lince, M., Perez, A. E. (1981) Mechanism of action of contraceptive synthetic progestins. J. Steroid Biochem. 15:125–130.

Perez–Palacios, G., Chavez, B., Vilchis, F., Escobar, N., Larrea, F., Perez, A. E. (1983)Interaction of medroxyprogesterone acetate with cytosol androgen receptors in the rat hypothalamus and pituitary. J. Steroid Biochem 19:1729–1735.

Podratz, K. C., O'Brien, P. C., Malkasian, G. D. Jr, Decker, D. G., Jefferies, J. A., Edmonston, J. H. (1985) Effects of progestational agents in treatment of endome- (List continued on next page.)

OTHER PUBLICATIONS trial carcinoma. Obstet. Gynecol. 66:106–110.

Poulin, R., Baker, D., Poirier, D., Labrie, F. (1990) Multiple action of synthetic progestins on the growth of ZR-75-1 human breast cancer cells: An in vivo model for the simultaneous assay of androgen, progestin, estrogen, and glucocotricoid agonistic and antagonistic activities of steroids. Br. Cancer Res. Treatm. 1:197–210.

Poulin, R., Baker, D., Labrie, F. (1988) Androgens inhibit basal and estrogen-induced cell proliferation in the ZR-75-1 human breast cancer cell line. Breast Cancer Res. Treatm. 12:213–225.

Poulin, R., Baker, D., Poirier, D., Labrie, F. (1989) Androgen and glucocorticoid receptor-mediated inhibition of cell proliferation by medroxyprogesterone acetate in ZR-75-1 human breast cancer cells. Breast Cancer Res. Treatm. 13:161–172.

Poulin, R., Labrie, F. (1986) Stimulation of cell proliferation and estrogenic response by adrenal C19-$\Delta$5-steroids in the ZR-75-1 human breast cancer cell line. Cancer Res. 46:4933–4937.

Preston, S. N. (1965) Pelvic endometriosis. Treatment with methyl testosterone. Obstet. Gynecol. 2:152–157.

Pridjian, G., Schmit, V., Schreiber, J. (1987) Medroxyprogestrone acetate: receptor binding and correlated effects on steroidogenesis in rat granulosa cells. J. Steroid Biochem. 26:313–319.

Roadbad, D. and Lewald, J. E. (1970) Computer analysis of radioligand assay and radioimmunoassay data. In: 2nd Symposium. Steroid Assay by Prolactin Binding. Karolinska Symposia on Research Methods in Reproductive Endocrinology, Geneva, pp. 79–103.

Said, S., Sadek, W., Knoleif, A., Koetsawang, S., Kifiwat, O., et al. (1988) A multicentred phase III comparative study of two hormonal contraceptive preparations given once-a-month by intramuscular injection: I. Contraceptive efficacy and side effects. Contraception 37:12.

Silberberg, M. and Silberberg, R. (1971) Steroid hormones and bone. Edited by G. H. Bourne GH. In:The biochemistry and physiology of bone. New YOrk, Academic Press, vol. II, 2nd ed, pp. 401–484.

Sledge, G. W., McGuire, W. L. (1983) Steroid hormone receptors in human breast cancer. Adv. Cancer Res. 38:61–75.

Tatman, J. L., Freedman, R. S., Scott, W., Atkinson, E. N. (1989) Treatment of advanced endometrial adenocarcinoma with cyclic sequential ethinyl estradiol and medroxyprogesterone acetate. Eur. J. Cancer Clin. Oncol. 25:1619–1621.

Urist, M. R., Vincent, P. J. (1961) The excretion of various fractions of the 17-ketosteroids in the urine in women with postmenopausal or senile osteoporosis. J. Clin. Orthop. 18:199–208.

Verhas, M., Schoutens, A., L'Hermite-Baleriaux, M., Dourov, N., Verschaeren, A., Mone, M., Heilporn, A. (1986) The effect of orchidectomy on bone metabolism in aging rats. Calif. Tissue Res. 39: 74–77.

Vilchis, F., Chavez, B., Pérez, A. E., Garcia, G. A., Angeles, A., Pérez-Palacios G. (1986) Evidence that a non-aromatizable metabolite of norethisterone induces estrogen-dependent pituitary progestin receptors. J. Steroid Biochem. 24: 525–531.

Van Veelen, H., Willemse, P. H. B., Sleijfer, D. T., van der Ploeg, E., Sluiter, W. J., Doorenbos, H. (1985) Mechanism of adrenal suppression by high-dose medroxyprogesterone acetate in breast cancer patients. Cancer Chemother. Pharmacol. 15: 167–170.

Wink C S, Felts W J L (1980) Effects of castration on the bone structure of male rats: a model of osteoporosis. Calcif. Tissue Int. 32: 77–82.

Wise, D. L., Fellmann, T. D., Sanderson, J. E., Wentworth, R. L. (1979) Lactic/Glycolic Acid Polymers. In: Biology and Medicine. Edited by G. Gregotiadis. Academic Press, New York, pp. 237–170.

Young, P. C. M., Keen, F. K., Einhorn, L. H., Stanich, B. M., Ehrlich, C. E., Cleary, R. E. (1980) Binding of medroxyprogesterone acetate in human breast cancer. Am. J. Obstet Gynecol. 137: 284–292.

CONTROLLED RELEASE SYSTEMS AND LOW DOSE ANDROGENS

RELATED APPLICATION

The application is a continuation-in-part of U.S. patent application Ser. No. 07/724,532 filed Jun. 28, 1991, and now abandoned.

FIELD OF THE INVENTION

This invention relates to a method for treating or preventing breast and endometrial cancer, bone loss, and for treating endometriosis in susceptible warm-blooded animals including humans involving administration of a compound possessing androgenic activity, and to kits containing active ingredients to be used in the therapy. Novel sustained release formulations and methods for their production and use are disclosed. Some preferred embodiments to novel formulations of injectable forms of medroxyprogesterone acetate and megestrol acetate which yield predetermined circulating levels of active ingredients for prolonged periods of time. Biodegradable microparticles are provided which release, for example, medroxyprogesterone acetate and megestrol acetate, at a near constant and slow rate when injected to warm-blooded animals including the human for the prevention and treatment of diseases as well as fertility control. Novel methods for removing undesirable residual solvent from sustained release particles are also provided.

BACKGROUND OF THE INVENTION

Various investigators have been studying hormonal therapy for breast and endometrial cancer as well as for the prevention and treatment of bone loss and for treatment of endometriosis. The main approaches for the treatment of already breast cancer are related to the inhibition of estrogen action and/or formation. The role of estrogens in promoting the growth of estrogen-sensitive breast cancer is well recognized (Lippman, Semin. Oncol. 10 (suppl. 4): 11-19, 1983; Sledge and McGuire, Cancer Res. 38: 61-75, 1984; Wittliff, Cancer 53: 630-643, 1984; Poulin and Labrie, Cancer Res. 46: 4933-4937, 1986).

Estrogens are also known to promote the proliferation of normal endometrium. Chronic exposure to estrogens unopposed by progesterone can lead to the development of endometrial hyperplasia which predisposes to endometrial carcinoma (Lucas, Obstet. Gynecol. Surv. 29: 507-528, 1974). The incidence of endometrial cancer increases after menopause, especially in women receiving estrogen therapy without simultaneous treatment with progestins (Smith et al., N. Engl. J. Med. 293: 1164-1167, 1975; Mack et al., N. Engl. J. Med. 294: 1262-1267, 1976).

Various investigators have been studying hormone-dependent breast and endometrial cancer. A known form of endocrine therapy in premenopausal women is castration most commonly performed by surgery or irradiation, two procedures giving irreversible castration. Recently, a reversible form of castration has been achieved by utilizing Luteinizing Hormone-Releasing Hormone Agonists (LHRH agonists) which, following inhibition of secretion of bioactive Luteinizing Hormone (LH) by the pituitary gland, decrease serum estrogens to castrated levels (Nicholson et al., Brit. J. Cancer 39: 268-273, 1979).

Several studies show that treatment of premenopausal breast cancer patients with LHRH agonists induces responses comparable to those achieved with other forms of castration (Klijn et al., J. Steroid Biochem. 20: 1381, 1984; Manni et al., Endocr. Rev. 7: 89-94, 1986). Beneficial effects of treatment with LHRH agonists have also been observed in postmenopausal women (Nicholson et al., J. Steroid Biochem. 23: 843-848, 1985).

U.S. Pat. No. 4,071,622 relates to the use of certain LHRH agonists against DMBA-induced mammary carcinoma in rats.

U.S. Pat. No. 4,775,660 relates to the treatment of female breast cancer by use of a combination therapy comprising administering an antiandrogen and an antiestrogen to a female after the hormone output of her ovaries has been blocked by chemical or surgical means.

U.S. Pat. No. 4,775,661 relates to the treatment of female breast cancer by use of a therapy comprising administering to a female, after the hormone output of her ovaries has been blocked by chemical or surgical means, an antiandrogen and optionally certain inhibitors of sex steroid biosynthesis.

U.S. Pat. No. 4,760,053 describes a treatment of selected sex steroid dependent cancers which includes various specified combinations of compounds selected from LHRH agonists, antiandrogens, antiestrogens and certain inhibitors of sex steroid biosynthesis.

In U.S. Pat. No. 4,472,382 relates to treatment of prostatic adenocarcinoma, benign prostatic hypertrophy and hormone-dependent mammary tumors with specified pharmaceuticals or combinations. Various LHRH agonists and antiandrogens are discussed.

WIPO International Publication WO921 0573 discuss certain 16,16 disubstituted androstene steroid compounds for hair growth and skin disorders. International Patent Application PCT/WO86/01105, discloses a method of treating sex steroid dependent cancers in warm-blooded animals which comprises administering specific pharmaceuticals and combinations. Antiandrogens, antiestrogens, certain inhibitors of sex steroid biosynthesis and blocking of hormonal output are discussed.

The inventor's U.S. patent application Ser. No. 07/321926 filed Mar. 10, 1989 and now abandoned, relates to a method of treatment of breast and endometrial cancer in susceptible warm-blooded animals which may include inhibition of ovarian hormonal secretion by surgical means (ovariectomy) or chemical means (use of an LHRH agonist, e.g. [D-Trp$^6$, des-Gly-NH$_2$$^{10}$]LHRH ethylamide, or antagonists) as part of a combination therapy. Antiestrogens, androgens, progestins, inhibitors of sex steroid formation (especially of 17$\beta$-hydroxysteroid dehydrogenase- or aromatase-catalyzed production of sex steroids), inhibitors of prolactin secretion and of growth hormone secretion and ACTH secretion are discussed.

Androgen receptors have been shown to be present in normal (Witliff, In: Bush, H. (Ed.), Methods in Cancer Res., Vol. 11, Acad. Press, New York, 1975, pp. 298-304; Allegra et al. Cancer Res. 39: 1447-1454, 1979) and neoplastic (Allegra et al., Cancer Res. 39: 1147-1454, 1979; Engelsman et al., Brit. J. Cancer 30: 177-181, 1975; Moss et al., J. Ster. Biochem. 6: 743-749, 1975; Miller et al., Eur. J. Cancer Clin. Oncol. 2: 539-542, 1985; Lippman et al., Cancer 38: 868-874, 1976; Allegra et al., Cancer Res. 39: 1447-1454, 1979; Miller et al., Eur. J. Clin. Oncol. 21: 539-542, 1985; Lea et al., Cancer Res. 49: 7162-7167, 1989) as well as in several established breast cancer cell lines (Lippman et al., Cancer Res. 36: 4610-4618, 1976; Horwitz et al., Cancer Res. 38: 2434-2439, 1978; Poulin et al., Breast Cancer Res. Treatm. 12: 213-225, 1988). Androgen receptors are also present in dimethylbenz(a)anthracene (DMBA)-induced mammary tumors in the rat (Asselin et al., Cancer Res. 40: 1612-1622, 1980).

Androgen receptors have also been described in human endometrium (MacLaughlin and Richardson, J. Steroid Biochem. 10: 371-377, 1979; Muechler and Kohler, Gynecol. Invest. 8: 104, 1988). The growth inhibitory effects of the androgen methyltrienolone (R1881), on endometrial carcinoma in vitro have been described (Centola, Cancer Res. 45: 6264-6267, 1985).

Recent reports have indicated that androgen receptors may add to the selective power of estrogen receptors or even supplant estrogen receptors as best predicting response to endocrine therapy (Teulings et al., Cancer Res. 40: 2557-2561, 1980; Bryan et al., Cancer 54: 2436-2440, 1984).

The first androgen successfully used in the treatment of advanced breast cancer is testosterone propionate (Nathanson, Rec. Prog. Horm. Res. 1: 261-291, 1947). Many studies subsequently confirmed the beneficial effect of androgens on breast cancer (Alan and Herrman, Ann. Surg. 123: 1023-1035; Adair, Surg. Gynecol. Obstet. 84: 719-722, 1947; Adair et al., JAMA 140: 1193-2000, 1949). These initial results stimulated cooperative studies on the effect of testosterone propionate and DES which were both found to be effective in producing objective remissions. (Subcommittee on Steroid and Cancer of the Committee on Research of the Council on Pharmacy and Chemistry of the Am. Med. Association followed by the Cooperative Breast Cancer Group under the Cancer Chemotherapy National Service Center of the NCI who found that testosterone propionate improved remission rate and duration, quality of life and survival (Cooperative Breast Cancer Group, JAMA 188, 1069-1072, 1964)).

A response rate of 48% (13 of 27 patients) was observed in postmenopausal women who received the long-acting androgen methonolone enanthate (Kennedy et al., Cancer 21: 197-201, 1967). The median duration of survival was four times longer in the responders as compared to the non-responder group (27 versus 7.5 months). A large number of studies have demonstrated that androgens induce remission in 20 to 40% of women with metastatic breast cancer (Kennedy, Hormone Therapy in Cancer. Geriatrics 25: 106-112, 1970; Goldenberg et al., JAMA 223: 1267-1268, 1973).

A response rate of 39% with an average duration of 11 months has recently been observed in a group of 33 postmenopausal women who previously failed or did not respond to Tamoxifen (Manni et al., Cancer 48: 2507-2509, 1981) upon treatment with Fluoxymesterone (Halostatin) (10 mg, b.i.d.). Of these women, 17 had also undergone hypophysectomy. There was no difference in the response rate to Fluoxymesterone in patients who had previously responded to Tamoxifen and in those who had failed. Of the 17 patients who had failed to both Tamoxifen and hypophysectomy, 7 responded to Fluoxymesterone for an average duration of 10 months. Among these, two had not responded to either Tamoxifen or hypophysectomy.

The combination Fluoxymesterone and Tamoxifen has been shown to be superior to Tamoxifen alone. In fact, complete responses (CR) were seen only in the combination arm while 32% showed partial response (PR) in the combination arm versus only 15% in the monotherapy arm. In addition, there were only 25% of non-responders in the combination therapy arm versus 50% in the patients who received TAM alone (Tormey et al., Ann. Int. Med. 98: 139-144, 1983). Moreover, the median time from onset of therapy to treatment failure was longer with Fluoxymesterone+Tamoxifen (180 days) compared to the Tamoxifen arm alone (64 days). There was a tendency for improved survival in the combination therapy arm (380 versus 330 days).

The independent beneficial effect of an androgen combined with an antiestrogen is suggested by the report that patients who did not respond to Tamoxifen could respond to Fluoxymesterone and vice versa. Moreover, patients treated with Tamoxifen and crossing over to Fluoxymesterone survived longer that those treated with the reverse regimen (Torney et al., Ann. Int. Med. 98: 139-144, 1983).

Since testosterone propionate had beneficial effects in both pre-and post-menopausal women (Adair et al., J. Am. Med. Ass. 15: 1193-1200, 1949), it indicates that in addition to inhibiting gonadotropin secretion, the androgen exerts a direct inhibitory effect on cancer growth.

Recent in vitro studies describe the relative antiproliferative activities of an androgen on the growth of the estrogen-sensitive human mammary carcinoma cell line ZR-75-1 (Poulin et al. "Androgens inhibit basal and estrogen-induced cell proliferation in the ZR-75-1 human breast cancer cell line", Breast Cancer Res. Treatm. 12: 213-225, 1989). As mentioned above, Poulin et al. (Breast Cancer Res. Treatm. 12: 213-225, 1989) have found that the growth of ZR-75-1 human breast carcinoma cells in inhibited by androgens, the inhibitory effect of androgens being additive to that of an antiestrogen. The inhibitory effect of androgens on the growth of human breast carcinoma cells ZR-75-1 has also been observed in vivo in nude mice (Dauvois and Labrie, Cancer Res. 51: 3131-3151, 1991).

As a possible mechanism of androgen action in breast cancer, it has recently been shown that androgens strongly suppress estrogen (ER) and progesterone (PgR) receptor contents in Zr-75-1 human breast cancer cells as measured by radioligand binding and anti-ER monoclonal antibodies. Similar inhibitory effects were observed on the levels of ER mRNA measured by ribonuclease protection assay. The androgenic effect is measured at subanomolar concentrations of the non-aromatizable androgen 5α-dihydrotestosterone, regardless of the presence of estrogens, and is competitively reversed by the antiandrogen hydroxyflutamide (Poulin et al., Endocrinology 125: 392-399, 1989). Such data on estrogen receptor expression provide an explanation for at least part of the antiestrogenic effects of androgens on breast cancer cell growth and moreover suggest that the specific inhibitory effects of androgen therapy could be additive to the standard treatment limited to blockade of estrogens by antiestrogens.

Dauvois et al. (Breast Cancer Res. Treatm. 14: 299-306, 1989) have shown that constant release of the androgen 5α-dihydrotestosterone (DHT) in ovariectomized rats bearing DMBA-induced mammary carcinoma caused a marked inhibition of tumor growth induced by 17β-estradiol ($E_2$). That DHT acts through interaction with the androgen receptor is supported by the finding that simultaneous treatment with the antiandrogen Flutamide completely prevented DHT action.

Particularly illustrative of the potent inhibitory effect of the androgen DHT on tumor growth are the decrease by DHT of the number of progressing tumors from 69.2% to 29.2% in $E_2$- treated animals and the increase by the androgen of the number of complete responses (disappearance of palpable tumors) from 11.5% to 33.3% in the same groups of animals. The number of new tumors appearing during the 28-day observation period in estradiol-treated animals decreased from 1.5±0.3 to 0.7±0.2 per rat during treatment with the androgen DHT, an effect which was also reversed by the antiandrogen Flutamide. Such data demostrate, for the first time, that androgens are potent inhibitors of DMBA-induced mammary carcinoma growth by an action independent from inhibition of gonadotropin secretion and suggest an action exerted directly at the tumor level, thus further supporting the in vitro data obtained with human ZR-75-1 breast cancer cells (Poulin et al., Breast Cancer Res. Treatm. 12: 213–225, 1988).

The natural androgens testosterone (TESTO) and dihydrotestosterone (DHT) are formed from conversion of androstenedione into TESTO by $17\beta$-hydroxysteroid dehydrogenase and then TESTO into DHT by the action of the enzyme $5\alpha$-reductase. The adrenal precursor 5-androst-5-ene-$3\beta$, $17\beta$-diol can also be converted into TESTO by action of the enzyme $3\beta$-hydroxysteroid dehydrogenase/$\Delta^5\Delta^4$ isomerase ($3\beta$-HSD).

Since the natural androgens TESTO and DHT have strong masculinizing effects, numerous derivatives of TESTO as well as progesterone have been synthesized in order to obtain useful compounds having fewer undesirable masculinizing side effects (body hair growth, loss of scalp hair, acne, seborrhea and loud voice).

Medroxyprogesterone acetate (MPA) is one of the most widely used compounds in the endocrine therapy of advanced breast cancer in women (Mattsson, Breast Cancer Res. Treatm. 3: 231–235, 1983; Blumenschein, Semin. Oncol. 10: 7–10, 1983; Hortobagyi et al., Breast Cancer Res. Treatm. 5: 321–326, 1985; Haller and Glick, Semin. Oncol. 13: 2–8, 1986; Horwitz, J. Steroid Biochem. 27: 447–457, 1987). The overall clinical response rate of high doses of this synthetic progestin averages 40% in unselected breast cancer patients (Horwitz, J. Steroid Biochem. 27: 447–457, 1987), an efficacy comparable to that of the non-steroidal antiestrogen tamoxifen (Lippman, Semin. Oncol. 10 (Suppl.): 11–19, 1983). Its more general use, however, is for breast cancer relapsing after other endocrine therapeutic modalities. The maximal inhibitory action of medroxyprogesterone acetate (MPA) on human breast cancer cell growth in vitro may be achieved at concentration as low as 1 nM while an approximately 1000-fold higher dose is often required for glucocorticoid action (Poulin et al., Breast Cancer Res. Treatm. 13: 161–172, 1989).

Until recently, the mechanisms underlying the antitumor activity of MPA were poorly understood and have been attributed to interaction with the progesterone receptor. This steroid, however, presents a high affinity for progesterone (PgR) as well as for androgen (AR) and glucocorticoid receptors (GR) in various animal tissues (Perez-Palacios et al., J. Steroid Biochem. 19: 1729–1735, 1983; Janne and Bardin, Pharmacol. Rev. 36: 35S–42S, 1984; Pridjian et al., J. Steroid Biochem. 26: 313–319, 1987; Ojasso et al., J. Steroid Biochem. 27: 255–269, 1987) as well as in human mammary tumors (Young et al., Am. J. Obstet. Gynecol. 137: 284–292, 1980), a property shared with other synthetic progesterone derivatives (Bullock et al., Endocrinology 103: 1768–1782, 1978; Janne and Bardin, Pharmacol. Rev. 36: 35S–42S, 1984; Ojasso et al., J. Steroid Biochem. 27: 255–269, 1987). It is known that in addition to progesterone receptors (PgR), most synthetic progestational agents bind with significant affinity to androgen (AR) as well as glucocorticoid (GR) receptors, and induce biological actions specifically determined by these individual receptor systems (Labrie et al., Fertil. Steril. 28: 1104–1112, 1977; Engel et al., Cancer Res. 38: 3352–3364, 1978; Raynaud et al., In: Mechanisms of Steroid Action (G. P. Lewis, M. Grisburg, eds), MacMiland Press, London, pp. 145–158, 1981; Rochefort and Chalbos, Mol. Cell. Endocrinol. 36: 3–10, 1984; Jänne and Bardin, Pharmacol. Rev. 36: 35S–42S, 1984; Poyet and Labrie, Mol. Cell. Endocrinol. 42: 283–288, 1985; Poulin et al., Breast Cancer Res. Treatm. 13: 161–172, 1989). Accordingly, several side effects other than progestational have been noted in patients treated with MPA.

The inhibitory effect of MPA on gonadotropin secretion is clearly exerted through its direct interaction with pituitary AR in the rat (Labrie et al., Fertil. Steril. 28: 1104–1112, 1977; Perez-Palacios et al., J. Steroid Biochem. 19: 1729–1735, 1983) and human (Perez-Palacios et al., J. Steroid Biochem. 15: 125–130, 1981). In addition, MPA exhibits androgenic activity in the mouse kidney (Janne and Bardin, Pharmacol. Rev. 36: 35S–42S, 1980) and in the rat ventral prostate (Labrie, C. et al., J. Steroid Biochem. 28: 379–384, 1987; Labrie C. et al., Mol. Cell. Endocrinol. 68: 169–179, 1990). Despite its high affinity for AR, MPA seldom causes significant virilizing symptoms (acne, hirsutism, etc.) (Haller and Glick, Semin. Oncol. 13, 2–8, 1986).

The most easily explained adverse side effects of MPA are related to its glucocorticoid-like action with Cushingoid syndrome, euphoria and subjective pain relief (Mattsson, Breast Cancer Res. Treatm. 3: 231–235, 1983; Blossey et al., Cancer 54: 1208–1215, 1984; Hortobagyi et al., Breast Cancer Res. Treatm. 5: 321–326, 1985; Van Veelan et al., Cancer Chemother. Pharmacol. 15: 167–170, 1985). Suppression of adrenal function by MPA is believed to be caused both by an inhibitory action on ACTH secretion at the pituitary level and by direct inhibition of steroidogenesis at the adrenal level (Blossey et al., Cancer 54: 1208–1215, 1984; Van Veelen et al., Cancer Chemother. Pharmacol. 15: 167–170, 1985; Van Veelen et al., Cancer Treat. Rep. 69: 977–983, 1985).

Despite its high affinity for AR, MPA seldom causes significant virilizing symptoms (acne, hirsutism, etc.) (Haller and Glick, Semin. Oncol. 13: 2–8, 1986). Moreover, its inhibitory effect on gonadotropin secretion is clearly exerted through its direct interaction with pituitary AR in the rat (Labrie et al., Fertil. Steril. 28: 1104–1112, 1977; Perez-Palacios et al., J. Steroid Biochem. 19: 1729–1735, 1983) and human (Perez-Palacios et al., J. Steroid Biochem. 15: 125–130, 1981). In addition, MPA exhibits androgenic activity in the mouse kidney (Jänne and Bardin, Pharmacol. Rev. 36: 35S–42S, 1980) and in the rat ventral prostate (Labrie, C. et al., J. Steroid Biochem. 28: 379–384, 1987; Labrie C. et al., Mol. Cell. Endocrinol. 68: 169–179, 1990).

Poulin et al. "Androgen and glucocorticoid receptor-mediated inhibition of cell proliferation by medroxyprogesterone acetate in ZR-75-1 human breast cancer cells", Breast Cancer Res. Treatm. 13: 161–172, 1989) have recently found that the inhibitory effect of medroxyprogesterone acetate (MPA) on the growth of the human ZR-75-1 breast cancer cells is mainly due to the androgenic properties of the compound. The androgenic properties of MPA have been demonstrated in other systems (Labrie C. et al., J. Steroid Biochem. 28: 379-384, 1987; Luthy et al., J. Steroid Biochem. 31: 845-852, 1988; Plante et al., J. Steroid Biochem. 31: 61-64, 1988; Labrie C. et al., Mol. Cell. Endocrinol. 58: 169-179, 1990). Other synthetic progestins have also been shown to possess, in addition to their progesterone-like activity, various degrees of androgenic activity (Labrie et al., Fertil. Steril. 31: 29-34, 1979; Poyet and Labrie, The Prostate 9: 237-246, 1986; Labrie C. et al., J. Steroid Biochem. 28: 379-384, 1987; Luthy et al., J. Steroid Biochem. 31: 845-852, 1988; Plante et al., J. Steroid Biochem. 31: 61-64, 1989).

High dose progestins, especially medroxyprogesterone acetate and megestrol acetate have also been successfully used for the treatment of endometrial cancer (Tatman et al., Eur. J. Cancer Clin. Oncol. 25: 1619-1621, 1989; Podratz et al., Obstet, Gynecol. 66: 106-110, 1985; Ehrlich et al., Am. J. Obstet. Gynecol, 158: 797-807, 1988). The androgen methyltesiosterone has been shown to relieve the symptoms of endometriosis (Hamblen, South Med. J. 50: 743, 1987; Preston, Obstet. Gynecol. 2: 152, 1965). Androgenic and masculinizing side effects (sometimes irreversible) are however important with potent androgenic compounds such as testosterone and its derivatives.

High dose MPA as first treatment of breast cancer has shown similar effects as Tamoxifen (Van Veelen et al., Cancer 58: 7-13, 1986). High dose progestins, especially medroxyprogesterone acetate and megestrol acetate have also been successfully used for the treatment of endometrial cancer (Tatman et al., Eur. J. Cancer Clin. Oncol. 25: 1619-1621, 1989; Podratz et al., Obstet. Gynecol. 66: 106-110, 1985; Ehrlich et al., Am. J. Obstet. Gynecol. 158: 797-807, 1988). High dose MPA is being used with a success similar to that of Tamoxifen for the treatment of endometrial carcinoma (Rendina et al., Europ. J. Obstet. Gynecol. Reprod. Biol. 17: 285-291, 1984).

In a randomized clinical trial, high dose MPA administered for 6 months has been shown to induce resolution of the disease in 50% of the patients and a partial resolution in 13% of subjects compared to 12% and 6%, respectively, in patients who received placebo (Telimaa et al., Gynecol. Endocrinol. 1: 13, 1987).

The androgen methyltestosterone has been shown to relieve the symptoms of endometriosis (Hamblen, South Med. J. 50: 743, 1987; Preston, Obstet. Gynecol. 2: 152, 1965). Androgenic and masculinizing side effects (sometimes irreversible) are however important with potent androgenic compounds such as testosterone.

In analogy with the androgen-induced decrease in estrogen receptors in human breast cancer ZR-75-1 cells (Poulin et al., Endocrinology 125: 392-399, 1989), oral administration of MPA to women during the follicular phase caused a decrease in the level of estrogen binding in the endometrium (Tseng and Gurpide, J. Clin. Endocrinol. Metab. 41, 402-404, 1975).

Studies in animals have shown that androgen deficiency leads to osteopenia while testosterone administration increases the overall quantity of bone (Silberberg and Silberberg, 1971; see Finkelstein et al., Ann. Int. Med. 106: 354-361, 1987). Orchiectomy in rats can cause osteoporosis detectable within 2 months (Winks and Felts, Calcif. Tissue Res. 32: 77-82, 1980; Verhas et al., Calif. Tissue Res. 39: 74-77, 1986).

While hirsute oligomenorrheic and amenorrheic women having low circulating $E_2$ levels would be expected to have reduced bone mass, these women with high androgen (but low estrogen) levels are at reduced risk of developing osteoporosis (Dixon et al., Clinical Endocrinology 30: 271-277, 1989).

Adrenal androgen levels have been found to be reduced in osteoporosis (Nordin et al., J. Clin. Endocr. Metab. 60: 651, 1985). Moreover, elevated androgens in postmenopausal women have been shown to protect against accelerated bone loss (Deutsch et al., Int. J. Gynecol. Obstet. 25: 217-222, 1987; Aloia et al., Arch. Int. Med. 143: 1700-1704, 1983). In agreement with such a role of androgens, urinary levels of androgen metabolites are lower in postmenopausal symptomatic menopausis than in matched controls and a significant decrease in conjugated dehydroepiandrosterone (DHEA) was found in the plasma of osteoporotic patients (Hollo and Feher, Acta Med. Hung. 20: 133, 1964; Urist and Vincent, J. Clin. Orthop. 18: 199, 1961; Hollo et al., Acta Med. Hung. 27: 155, 1970). It has even been suggested that postmenopausal osteoporosis results from both hypoestrogenism and hypoandrogenism (Hollo et al., Lancet: 1357, 1976).

As a mechanism for the above-suggested role of both estrogens and androgens in osteoporosis, the presence of estrogen (Komm et al., Science 241: 81-84, 1988; Eriksen et al., Science 241: 84-86, 1988) as well as androgen (Colvard et al., Proc. Natl. Acad. Sci. 86: 854-857, 1989) receptors in osteoblasts could explain increased bone resorption observed after estrogen and androgen depletion.

In boys, during normal puberty, an increase in serum testosterone levels procedes an increase in alkaline phosphate activity (marker of osteoblastic activity) which itself precedes increased bone density (Krabbe et al., Arch. Dis. Child. 54: 950-953, 1979; Krabbe et al., Arch. Pediat. Scand. 73: 750-755, 1984; Riis et al., Calif. Tissue Res. 37: 213-217, 1985).

While, in women, there is a rapid bone loss starting at menopause, bone loss in males can be recognized at about 65 years of age (Riggs et al., J. Clin. Invest. 67: 328-335, 1987). A significant bone loss is seen in men at about 80 years of age, with the accompanying occurrence of hip, spine and wrist fractures. Several studies indicate that osteoporosis is a clinical manifestation of androgen deficiency in men (Baran et al., Calcif. Tissue Res. 26: 103-106, 1978; Odell and Swerdloff, West. J. Med. 124: 446-475, 1976; Smith and Walker, Calif. Tissue Res. 22 (Suppl.): 225-228, 1976).

Although less frequent than in women osteoporosis can cause significant morbidity in men (Seeman et al., Am. J. Med. 75: 977-983, 1983). In fact, androgen deficiency is a major risk for spinal compression in men (Seeman et al., Am. J. Med. 75: 977-983, 1983). Decreased radial and spinal bone density accompanies hypogonadism associated with hyperprolactinernia (Greespan et al., Ann. Int. Med. 104: 777-782, 1986) or anaorexia nervosa (Rigotti et al., JAMA 256: 385-288, 1986). However, in these cases, the role of hyperprolactinemia and loss in body weight is uncertain.

Hypogonadism in the male is a well-recognized cause of osteoporotic fracture (Albright and Reinfenstein, 1948; Saville, Clin. End. Metab. 2: 177-185, 1973). Bone density is in fact reduced in both primary and secondary hypogonadism (Velentzas and Karras. Nouv. Presse Médicale 10: 2520, 1981).

Severe osteopenia as revealed by decreased cortical and trabecular bone density was reported in 23 hypogonadotropic hypogonadal men (Finkelstein et al., Ann. Int. Med. 106: 354–361, 1987; Foresta et al., Horm. Metab. Res. 15: 56–57, 1983). Osteopenia has also been reported in men with Klinefelter's syndrome (Foresta et al., Horm. Metab. Res. 15: 206–207, 1983; Foresta et al., Horm. Metab. Res. 15: 56–57, 1983; Smith and Walker, Calif. Tissue Res. 22: 225–228, 1977).

Androgenic-reversible decreased sensitivity to calcitonin has been described in rats after castration (Ogata et al., Endocrinology 87: 421, 1970; Hollo et al., Lancet 1: 1205, 1971; Hollo et al., Lancet 1: 1357, 1976). In addition, serum calcitonin has been found to be reduced in hypogonadal men (Foresta et al., Horm. Metab. Res. 15: 206–207, 1983) and testosterone therapy in castrated rats increases the hypocalcemic effect of calcitonin (McDermatt and Kidd, End. Rev. 8: 377–390, 1987).

Albright and Ruferstein (1948) originally suggested that androgens increase the synthesis of bone matrix. Androgens have also been shown to increase osteoid synthesis and mineralization in chicken (Puche and Rosmano, Calif. Tissue Res. 4: 39–47, 1969). Androgen therapy in hypogonadal men increases skeletal growth and maturation (Webster and Hogkins, Proc. Soc. Exp. Biol. Med. 45: 72–75, 1940). In addition, testosterone therapy in man has been shown to cause positive nitrogen, calcium and phosphate balance (Albright, F., Reifeinstein, E. C. In: The parathyroid glands and metabolic bone disease. Williams and Williams Co.: Baltimore, pp. 145–204, 1948). As studied by bone histomorphometry, testosterone therapy in hypogonadal males resulted in increases in relative osteoid volume, total osteoid surface, linear extend of bone formation and bone mineralization (Barau et al., Calcif. Tissue Res. 26: 103–106, 1978).

Treatment with testosterone has been shown to increase osteoid surfaces and beam width with unchanged or reduced oppositional rates, thus indicating and increase in total bone mineralization rate (Peacock et al., Bone 7: 261–268, 1986). There was also a decrease in plasma phosphate probably due to an effect on renal tubular reabsorption of phosphates (Selby et al., Clin. Sci. 69: 265–271, 1985).

Cortical bone density increases in hyperprolactinemic men with hypogonadism when testicular function is normalized (Greenspan et al., Ann. Int. Med. 104: 777–782, 1986; Greenspan et al., Ann. Int. Med. 110: 526–531, 1989). Testosterone therapy increases bone formation in men with primary hypogonadism (Baron et al., Calcif. Tissue Res. 26: 103–106, 1978). Francis et al., Bone 7: 261–268, 1986).

In 21 hypogonadal men with isolated GnRH deficiency, normalization of serum testosterone for more than 12 months increased bone density (Kinkelstein et al., J. Clin. Endocr. Metab. 69: 776–783, 1989). In men with already fused epiphyses, however, there was a significant increase in cortical bone density while no significant change was observed on trabecular bone density, thus supporting previous suggestions of variable sensitivity of cortical and trabecular bone to steroid therapy.

Previous studies with anabolic steroids in small numbers of patients have suggested positive effects on bone (Lafferty et al., Ann. J. Med. 36: 514–528, 1964; Riggs et al., J. Clin. Invest. 51: 2659–2663, 1972; Harrison et al., Metabolism 20: 1107–1118, 1971). More recently, using total body calcium measurements by neutron activation as parameter, the anabolic steroid methandrostenolone has shown positive and relatively long-term (24–26 months) effects in a double-blind study in postmenopausal osteoporosis (Chessnut et al., Metabolism 26: 267–277, 1977; Aloia et al., Metabolism 30: 1076–1079, 1981).

The anabolic steroid nandrolone decanoate reduced bone resorption in osteoporotic women (Dequeker and Geusens, Acta Endocrinol. 271 (Suppl.): 45–52, 1985) in agreement with the results observed during estrogen therapy (Dequeker and Ferin, 1976, see Dequeker and Geusens). Such data confirm experimental data in rabbits and dogs when nandrolone decanoate reduced bone resorption (Ohem et al., Curr. Med. Res. Opin. 6: 606–613, 1980). Moreover, in osteoporotic women (Dequeker and Geusens, Acta Endocrinol. (Suppl.) 271: 45–52, 1985) the anabolic steroid not only reduced bone loss but also increased bone mass. Vitamin D treatment, on the other hand, only reduced bone resorption.

Therapy of postmenopausal women with nandrolone increased cortical bone mineral content (Clin. Orthop. 225: 273–277). Androgenic side effects, however, were recorded in 50% of patients. Such data are of interest since while most therapies are limited to an arrest of bone loss, an increased in bone mass was found with the use of the anabolic steroid nandrolone. A similar stimulation of bone formation by androgens has been suggested in a hypogonadal male (Baran et al., Calcif. Tissue Res. 26: 103, 1978). The problem with regimens which inhibit bone resorption with calcium, calcitriol or hormones is that they almost certainly lead to suppression of bone formation (Need et al., Mineral. Electrolyte Metabolism 11: 35, 1985). Although, Albright and Reiferestein (1948) (See Need, Clin. Orthop. 225: 273, 1987) suggested that osteoporosis is related to decreased bone formation and will respond to testosterone therapy, the virilizing effects of androgens have made them unsuitable for the treatment of postmenopausal women. Anabolic steroids, compounds having fewer virilizing effects, were subsequently developed. Although, minimal effects have been reported by some (Wilson and Griffin, Metabolism 28: 1278, 1980) more positive results have been reported (Chessnut et al., Metabolism 32: 571–580, 1983; Chessnut et al., Metabolism 26: 267, 1988; Dequeker and Geusens, Acta Endocrinol. (Suppl. 110) 271: 452, 1985). A randomized study in postmenopausal women has been shown an increase in total bone mass during treatment with the anabolic steroid stanazolol although side effects were recorded in the majority of patients (Chessnut et al., Metabolism 32: 571–580, 1983).

As mentioned above, the doses of "progestins" (for example medroxyprogesterone acetate) used for the standard therapy of breast cancer are accompanied by undesirable important side effects (especially those related to interaction of the steroid with the glucocorticoid receptor, especially Cushingoid syndrome, euphoria) (Mattsson, Breast Cancer Res. Treatm. 3: 231–235, 1983; Blossey et al., Cancer 54: 1208–1215, 1984; Hortobagyi et al., Breast Cancer Res. Treatm. 5: 321–326, 1985; Von Veelen et al., Cancer Chemother. Pharmacol. 15: 167–170, 1985).

The term "progestin" refers to derivatives of progesterone and testosterone. Such progestins have, at times, been synthesized with the aim of developing compounds acting as analogs of progesterone on the progesterone receptors, especially for the control of fertility. With the availability of new and more precise tests, however, it became evident that such compounds, originally made to interact exclusively with the progesterone receptor, do also interact, frequently with high affinity, with the androgen receptor (Labrie et al., Fertil. Steril. 28: 1104–1112, 1977; Labrie et al., Fertil. Steril. 31: 29–34, 1979; Labrie, C. et al., J. Steroid Biochem. 28: 379–384, 1987; Labrie C. et al., Mol. Cell. Endocrinol. 68: 169–179, 1990). Sometimes, the androgenic activity of these compounds, especially at low concentrations, becomes more important than the true progestin activity. This is the case, for example, for medroxyprogesterone acetate (Poulin et al., Breast Cancer Res. Treatm. 13: 161–172, 1989).

A problem with prior-art treatments of breast and endometrial cancer with synthetic progestins is the side effects observed with such treatments. The blockade of estrogens, another common treatment for breast cancer, would have undesirable deleterious effects on bone mass in women. Similarly, blockade of estrogens, a common treatment for endometriosis, has similar undesirble deleterious effects on bone mass in women.

Contraceptive preparations which allow protection for extended periods of time have been developped over the last 25 years. This include steroids with intrinsic long action after injection (e.g. Depoprovera; or more recently, through the use of extrinsic delivery systems, e.g. implants, microspheres, vaginal rings, I.U.Ds., etc.). Today, MPA and norethisterone (NET)-enanthate are used in family planning programs. In 1985, it was estimated that 4 million women were taking MPA and almost one million NET-enanthate (Hall, P.E., Long-acting injectable preparations. Fertility Regulation, Today and Tomorrow (Diczfalusy, E., Bydeman, M., eds), Raven Press: New York, pp. 119–141, 1987). In addition, it is estimated that 0.5 million women in Latin America and 1.0 million women in China are taking various once-a-month injectable preparations containing one progestogen and an estrogen (Hall, 1987, same ref. as above). Contraceptive preparations which allow protection over extended periods of time have been developped over the last 25 years.

An overview of two long-acting contraceptive steroids is presented in Contraception, May 1977, vol. 15, no. 5, pp. 513–533.

Depoprovera (25 mg) in combination with 5 mg estradiol cypionate has been given once-a-month (injection) for fertility control (WHO, Said et al., Contraception, 37: 1–20, 1988) Little difference in efficacy and side effects was seen when comparing to the once-a-month injection of 50 mg norethisterone enanthate and 5 mg estradiol valerate. More than 10,000 women-month were studied in each group. The combination MPA-$E_2$ cypionate was highly effective as contraceptive since no pregnancy was observed out of 10,969 women-month. The discontinuation rate in women using a once-a-month injection was relatively high at 35% at one year (WHO, Said et al., Contraception 37: 11–20, 1988) while bleeding irregularities were involved in only about 6.1% and amenorrhea in 2.1% of women. Late for injection, personal reasons and lost to follow-up amounted to 18.6% of discontinuations. Such data indicate the need for more easily acceptable schedules of administration.

DepoMPA (also called Depoprovera) used alone (150 mg, I.M. every 3 months) in 20,498 women-month has shown a pregnancy rate of $0.1\pm0.1\%$ and $15.0\pm1.0\%$ bleeding irregularities with an $11.9\pm1.0\%$ incidence of amenorrhea (WHO, Said et al., Contraception 37: 1–20, 1988). In a smaller study (5434 women-month), DepoMPA, at the same dose, led to a discontinuation rate of $40.7\pm2.0\%$ while bleeding irregularities and amenorrhea occurred in $14.7\pm1.5\%$ of patients.

Previous use of MPA has been through oral administration or intramuscular injection (Depoprovera). Oral administration is limited by problems of compliance and fluctuating blood levels while release of MPA from Depoprovera injection is rapid at first and declines in a highly variable fashion at later time intervals. There is thus the need for a controlled release formulation of MPA which delivers constant amounts of the steroid for defined long time periods assuring patient's compliance and increasing efficacy through the delivery of constant blood levels of the drug to the tissue(s) in need of treatment. Similar arguments apply to MGA.

Microencapsulation drug delivery systems have been widely developed during the last thirty years for controlled release of therapeutic agents, especially by incorporation of the active agents into biodegradable polyesters such as poly($\epsilon$-caprolactone), poly($\epsilon$-caprolactone-CO-DL-lactic acid), poly(DL-lactic acid), poly(DL-lactic acid-CO-glycolic acid) and poly($\epsilon$-caprolactone-CO-glycolic acid). See, for example and references, R. W. Baker (R. W. Baker, Controlled release of biologically active agents, John Wiley and Sons Ed., N.Y., 1987.), F. Lim (F. Lim, Biomedical Application of Microencapsulation, Franklin Lim, Ed. CRC Press, BocaRaton, 1984)

In U.S. Pat. No. 3,773,919 G. A. Boswell and R. M. Scribner disclose the use a polylactide-drug mixtures, especially steroids such as medroxyprogesterone acetate, for slow sustained release of the drugs.

In DE 3 503 679, Carli discloses medroxyprogesterone acetate formulations by combining with water swellable water insoluble polymer.

In Wo 8 807 816, R. J. Leonard discloses fused recrystallised steroid drug pellet useful as sustained release implant.

In U.S. Pat. No. 4,818,542, DeLuca et al. disclose the use and making of porous microspheres for drug delivery.

In DE 2 010 115, Farbenfabriken Bayer AG disclose the preparation of solid sprayable microgranulates for retarded release of pharmaceuticals.

In U.S. Pat. No. 4,166,800, F. W. Fong disclose the production of microspheres by adding phase separation agent at low temperature.

In U.S. Pat. No. 4,897,268, Tice et al. disclose drug delivery system including poly(DL-lactide-co-glycolide) for encapsulation.

In U.S. Pat. No. 4,107,071, R. G. Bayless disclose the preparation of microcapsules of partially hydrolyzed copolymer of ethylene and vinyl acetate.

In DE 2 051 580, Du Pont and Co disclose the preparation of controlled release parenteral pellets.

In U.S. Pat. No. 4,622,244, Lapka et al. disclose the encapsulation of particulate or material with phase separation, and isolation of microcapsules at low temperature.

In U.S. Pat. No. 4,987,268, E. S. Nuwayser and W. A. Nucefora disclose the preparation a composite core microparticles.

Wise et al (D. L. Wise Lactic/ Glycolic Acid Polymers, Biology & Medicine, G. Gregotiadis ed., New York Academic Press, pp. 237–270, 1979.) describe the application of Lactic/Glycolic Acid (co)Polymers in medicine. See also Lewis, "Controlled Release of Bioactive Agents from Lactide/Glycolide Polymers", Drug and Pharmaceutical Sciences, vol. 45, pp. 1–41, 1990.

An injectable sustained release preparation containing norethisterone as the contraceptive steroid has shown uniform release for 2 months in the rat (Anderson et al., Contraception 13: 375–384, 1976). The cryogenically ground particles 90–180 μm in size contained 20% of norethisterone incorporated in a biodegradable polymer matrix synthesized from L(+)lactic acid to a molecular weight of 200,000. A preparation (powder of 90–180 μm particle size) containing 20% norethisterone in a polymer synthesized from 90 parts of L-lactide by weight and 10 parts of glycolide to a molecular weight of 200,000 released the compound for approximately 2 months in baboons (Gresser et al., Contraception 17: 253–266, 1978). However, the zero rate of release found in rats was not confirmed in this study performed in primate (Beck and Tice, In Long acting steroid contraception (D. R. Mishell, ed) Raven Press: New York, pp. 175–199, 1983). The injectable DL-PLANET microcapsule system is the only form that has been studied in detail under in vivo conditions (Review by Beck and Tice. In Long acting steroid contraception (D. R. Mishell, ed) Raven Press: New York, pp. 175–199, 1983).

Most of the techniques used for the preparation of microparticles need the use of organic solvents which remain present at a non negligible percentage and may cause local or systemic unwanted toxic effects. Other prior art techniques need the use of high temperature with potential unwanted thermal decomposition of the steroid and/or polymer.

A problem with prior-art treatments of breast and endometrial cancer with MPA and megestrol acetate is the side effects observed with such treatments. A problem with the use of derivatives of 19-nortestosterone such as norgestrel, norethisterone and norethindrone is that such compounds possess estrogenic activity (Vilchis et al., J. Ster. Biochem. 24: 525–531, 1986; Larrea et al. J. Ster. Biochem. 27: 657–663, 1987; Poulin et al., Breast Cancer Res. Treatm. 17: 197–210, 1990). Such estrogenic activity could well have a negative effect on breast cancer incidence over long-term use.

There is thus a need in the art of the treatment and prevention of estrogen-dependent diseases (as well as osteoporosis and contraception) of injectable long-acting delivery systems of medroxyprogesterone acetate and megestrol acetate which could maintain the circulating concentration of these steroids at a low level for long periods of time (e.g. 1 month and longer) and which contain negligible amounts of toxic residual organic solvent and/or thermal degradation impurities caused by exposing the therapeutic formulation to excessive heat.

Especially for contraceptive and preventive purpose, long-term delivery systems of MPA, MGA, or other androgenic compounds with negligible masculinizing activity should have a positive impact on costs of the health care system.

SUMMARY OF THE INVENTION

It is an object of the present invention to provide a method for prevention and treatment of breast cancer, endometrial cancer, osteoporosis and endometriosis, while substantially avoiding undesirable side effects.

It is another object of the invention to provide a method for prevention of bone loss in women where estrogen formation and/or action is blocked in order to treat various estrogen-sensitive diseases. Estrogen-sensitive diseases include any diseases whose onset, maintenance or progress is, at least in part, dependent upon biological activities induced by estrogens. For example, estrogen-related diseases include but are not limited to breast cancer, endometrial cancer, bone loss, endometriosis and osteoporosis.

It is another object of the invention to provide a method for prevention of bone loss in women already exposed to low estrogens following menopause.

It is a another object of the invention to provide kits and pharmaceutical compositions for use in the methods described herein.

It is another object of the present invention to provide microspheres or microparticles which maintain, in warm-blooded animals including humans, circulating concentrations of androgens at low levels for extended periods of time. Such particles are useful for contraception as well as for the purposes set forth above.

It is another object of the present invention to provide a method of using therapeutically effective amounts of controlled-release medroxyprogesterone acetate or megestrol acetate for treatment or prevention of estrogen-related diseases, while substantially avoiding undesirable side effects in humans and other mammals.

It is another object of the present invention to provide sustained-release microparticles or microspheres which contain low levels of residual organic solvent.

The above and other objects are achieved by practicing the methods disclosed herein and/or by utilizing the pharmaceutical compounds, compositions and kits disclosed herein.

In one embodiment, a method is provided for activating androgen receptors in a warm blooded animal, including a human, comprising administering to said animal at least one androgenic steroid having a Ki value of less than $2 \times 10^{-8}$M for the androgen receptor, an androgen receptor-mediated inhibitory effect on the growth of human breast cancer ZR-75-1 cells which reaches half-maximal value at a concentration below 3.0 nanomoles per liter, and no visible masculinizing activity at blood serum concentrations below 50 nM, wherein every such androgenic steriod is administered at a dosage sufficiently low to maintain a cumulative serum concentration below 50 nanomoles per liter.

The methods described herein are particularly useful for the treatment of human breast or endometrial cancer, osteoporosis or endometriosis. It is believed that the methods are also suitable for other purposes which are enhanced by administering androgens or otherwise activating androgen receptors. Both treatment and prevention of the diseases and disorders discussed herein are contemplated within the scope of the invention. It is believed that the methods of the invention are suitable for both prophylactic and therapeutic use.

In another embodiment, sustained release particles are provided which comprise an androgenic steroid of the invention wherein said androgenic steroid is dispersed within a sustained-release binder which is biocompatible with human tissue and which undergoes biodegradation in the body into biocompatible metabolic products, wherein said particles are capable, under standard conditions, of releasing said androgenic steroid during and as result of said biodegradation of said binder at a rate and duration which maintains circulating serum levels of said androgenic steroid between 1.0 and 50.0 nanomoles per liter during a time period beginning 48 hours after administration and ending at least 28 days after administration.

"Standard Conditions" for measuring ratio rate-of-release is described in the Detailed Description below. Rate-of-Release is an inherent property of the sustained release particles under defined conditions and is not a limitation on the manner in which such particles may be used. For example, the particles rate-of-release is defined at a certain dosage. However, the particles so defined may be used at a wide variety of different dosages as discussed in detail below and as deemed appropriate by the attending clinician. Other parameters such as method of administering the particles, duration of sustained release and the like may also be varied over a broad range as taught below. Pharmaceutical diluent or carrier may be added.

In another embodiment, a method of removing residual organic solvent from sustained release particles is provided and comprises the steps of
(A) Forming sustained release particles having an average size between 5 μm and 40 μm, said particles comprising an active compound dispersed within a sustained-release binder and undesirably including residual organic solvent, and then
(B) subjecting said particles to a strong vacuum wherein pressure is less than 1.0 torr and temperature is between 7° and 15° C. less than the glass transition temperature of said binder, for a time period sufficient to reduce residual organic solvent in said microspheres to a concentration of less than 0.1% (by weight, relative to total weight of said particles).

In another embodiment, a pharmaceutical composition is provided optionally comprising a pharmaceutically acceptable diluent or carrier and having a plurality of sustained release microspheres having an average size between 5 μm and 40 μm including an active agent dispersed within a sustained-release binder which is biocompatible with human tissues and which undergoes biodegradation in the body into biocompatible metabolic products, wherein said microspheres are capable, under standard conditions, of releasing said active agent, during and as a result of said biodegradation of said binder, over a period of at least 28 days, wherein said microspheres have no more than 0.1 percent (by weight relative to total weight of microspheres) of an organic solvent.

In another embodiment, the invention provides methods for treating or preventing estrogen sensitive diseases and disorders including but not limited to breast cancer, endometrial cancer, osteoporosis and endometriosis. The methods comprise administering to a patient in need of such treatment or prevention, an effective amount of sustained release particles, with or without additional pharmaceutical carriers or diluents, said particles comprising an androgenic steroid of the invention, (for example medroxyprogesterone acetate or megestrol acetate) wherein said androgenic steroid is dispersed within a sustained-release binder which is biocompatible with human tissue and which undergoes biodegradation in the body into biocompatible metabolic products, wherein said particles are capable, under standard conditions, of releasing said androgenic steroid during and as result of said biodegradation of said binder at a rate and duration which maintains circulating serum levels of said androgenic steroid between 1.0 and 50.0 nanomoles per liter during a time period beginning 48 hours after administration and ending at least 28 days after administration.

In another embodiment, a method of contraception is provided comprising administering to a female patient desiring contraception an effective amount of sustained release particles, with or without additional diluent or carriers, said particles, comprising medroxyprogesterone acetate dispersed within a sustained-release binder which is biocompatible with human tissue and which undergoes biodegradation in the body into biocompatible metabolic products, wherein said particles are capable, under standard conditions, of releasing said medroxyprogesterone acetate, during and as a result of said biodegradation, at a rate and duration which maintains circulating serum levels of said medroxyprogesterone acetate between 1.0 and 50.0 nanomoles per liter during a time period beginning 48 hours after administration and ending at least 28 days after administration, wherein said microspheres have no more than 0.1 percent (by weight relative to total weight of particles) of an organic solvent.

The androgens utilized have the special property of possessing potent androgenic activity at low blood concentration (e.g. less than 50 nM) while exhibiting very little glucocorticoid receptor activity at those concentrations. They are also characterized by the absence of physical masculinizing activity in females at the concentration range at which they are used. This is to be distinguished from natural androgens produced in gonadal or peripheral tissues such as testosterone and dihydrotestosterone which exhibit considerable masculinizing activity even at low blood concentrations. Synthetic progestins, e.g. progesterone derivatives are useful for this invention, as are some anabolic steroids.

The androgens of the invention on average do not cause physically detectable increase in masculinizing effects such as increased hair growth in females, acne, seborrhea or hair loss. These masculinizing effects have been quantified in the literature. See, for example, Ferriman and Gallwey, J. P. Clin. Endocrinol. Metab. 21: 1440–1447, 1961 (regarding hair growth); Cremoncini et. al., Acta. Eur. Fertil. 7: 248–314, 1976 (acne, seborrhea and hair loss). See also Cusan et. al., J. Am. Acad. Dermatol. 23: 462–469, 1990. Tables 1 and 2 below set forth a quantification.

TABLE 1

Definition of hair grading at each of 11 sites
(Grade 0 at all sites indicates absence of terminal hair)

| Site | Grade | Definition |
|---|---|---|
| 1. Upper lip | 1 | A few hairs at outer margin |
| | 2 | A small moustache at outer margin |
| | 3 | A moustache extending halfway from outer margin |
| | 4 | A moustache extending to mid-line |
| 2. Chin | 1 | A few scattered hairs |
| | 2 | Scattered hairs with small concentrations |
| | 3 & 4 | Complete cover, light and heavy |
| 3. Chest | 1 | Circumareolar hairs |
| | 2 | With mid-line hair in addition |
| | 3 | Fusion of these areas, with three-quarter cover |
| | 4 | Complete cover |
| 4. Upper back | 1 | A few scattered hairs |
| | 2 | Rather more, still scattered |
| | 3 & 4 | Complete cover, light and heavy |
| 5. Lower back | 1 | A sacral tuft of hair |

TABLE 1-continued

Definition of hair grading at each of 11 sites
(Grade 0 at all sites indicates absence of terminal hair)

| Site | Grade | Definition |
|---|---|---|
| | 2 | With some lateral extension |
| | 3 | Three-quarter cover |
| | 4 | Complete cover |
| 6. Upper abdomen | 1 | A few mid-line hairs |
| | 2 | Rather more, still mid-line |
| | 3 & 4 | Half and full cover |
| 7. Lower abdomen | 1 | A few mid-line hairs |
| | 2 | A mid-line streak of hair |
| | 3 | A mid-line band of hair |
| | 4 | An inverted V-shaped growth |
| 8. Arm | 1 | Sparse growth affecting not more than a quarter of the limb surface |
| | 2 | More than this; cover still incomplete |
| | 3 & 4 | Complete cover; light and heavy |
| 9. Forearm | 1,2,3,4 | Complete cover of dorsal surface; 2 grades of light and 2 of heavy growth |
| 10. Thigh | 1,2,3,4 | As for arm |
| 11. Leg | 1,2,3,4 | As for arm |

TABLE 2

Grading of Acne, Seborrhea and Hair Loss

| | Acne |
|---|---|
| 1. | Isolated pustules, up to 10 in number |
| 2. | More than 10 isolated pustules |
| 3. | Clusters of pustules |
| 4. | Confluent pustules |
| | Seborrhea |
| 1. | Mild |
| 2. | Moderate |
| 3. | Severe |
| | Hair Loss |
| 1. | Mild |
| 2. | Obvious thinning |
| 3. | Very obvious thinning |
| 4. | Baldness |

DETAILED DESCRIPTION OF THE PREFERRED EMBODIMENTS

Preferred compounds for use in the invention include synthetic progestins, anabolic steroids and other steroidal compounds having a Ki value of less than $2 \times 10^{-8}$M for the androgen receptor, and androgen receptor-mediated inhibitory effect on the growth of human breast cancer ZR-75-1 cells reaching half-maximal value at a concentration below 3.0 nanomoles per liter, and lacking the masculinizing activity discussed above. Preferred androgens of the invention would cause no significant increase in the average masculinizing effect (e.g. a significant increase in any of the numerical grades set forth in Tables 1 or 2 above) observed in females following treatment for three months with blood concentrations of the androgen maintained at the top of the claimed concentration range (e.g. 50 nanomoles per liter). For most female patients for whom no masculinizing effects were visible prior to treatment, or a total score of 10 or less for all 11 sites indicated in Table 1 prior to treatment, the same score would normally be maintained during treatment in accordance with the present invention. That is, there would be no visible masculinizing effects after three months of treatment. For female patients displaying some masculinizing effects prior to treatment, it would be expected that those effects would not be increased by treatment.

To determine whether the Ki values are below $2 \times 10^{-8}$M, Ki values may be determined by the following method for measuring the affinity of various compounds for the androgen receptor.

Preparation of prostatic tissue Ventral prostates are from Sprague-Dawley rats (Crl:CD(SD)Br) (obtained from Charles River, St-Constant, Québec) weighing 200-250 g and castrated 24 h before sacrifice. Immediately after removal, prostates are kept on ice and used for the androgen binding assays.

Preparation of cytosol Prostatic tissues are finely minced with scissors (fresh tissue) or pulverized with a Thermovac system (frozen tissue) before homogenization in buffer A (Tris, 0.025M; monothioglycerol, 20 mM; glycerol, 10% (v/v); EDTA, 1.5 mM and sodium molybdate, 10 mM, pH 7.4) in a 1:5 ratio (w/v) using a Polytron PT-10 homogenizer. These and all the following procedures are performed at 0°-4° C. The homogenate is centrifuged at $105000 \times g$ for 1 h in order to obtain the cytosolic fraction in the supernatant.

Cytosolic androgen receptor assay Aliquots of 100 μl are incubated at 0°-4° C. for 18 h with 100 μl of 3 nM [$^3$H]T or [$^3$H]R1881 in the presence or absence of increasing concentrations of the non-labeled androgenic compound to be tested. At the end of the incubation, free and bound T or R1881 are separated by the addition of 200 μl dextran-coated charcoal (1% charcoal, 0.1% dextran T-70, 0.1% gelatin, 1.5 mM EDTA and 50 mM Tris (pH 7.4)) for 15 min before centrifugation at $2300 \times g$ for another 15 min at 0°-4° C. Aliquots (350 μl) of the supernatant are transferred to scintillation vials with 10 ml of an aqueous counting solution (Formula 963, New England Nuclear) before counting in a Beckman LS 330 counter (30% efficiency for tritium).

Ki calculation Apparent inhibition constant "Ki" values are calculated according to the equation $Ki = IC_{50}/(1 + S/K)$ (Cheng and Prusoff, Biochem. Pharmacol. 22: 3099-3108, 1973). In this equation, S represents the concentration of [$^3$H]T or [$^3$H]R1881, K is the dissociation constant ($K_D$) of T or R1881 and $IC_{50}$ is the concentration of unlabeled compounds giving a 50% inhibition of T or R1881 binding. For numerous compounds, Ki values are reported in the literature. See, for example, Ojasso et al., J. Ster. Biochem. 27: 255-269, 1987; Asselin et al., Cancer Res. 40: 1612-1622, 1980; Toth and Zakar J. Steroid Biochem. 17: 653-660, 1982. A method giving similar results is described in Poulin et al., Breast Cancer Res. Treatm. 12: 213-225, 1988.

In order to determine the concentration at which a given compound reaches half-maximal androgen receptor-mediated inhibitory effect on the growth of human breast cancer ZR-75-1 cells, the following technique is utilized as described in detail in Poulin et al., Breast Cancer Res. Treatm. 12: 213-225, 1988.

Maintenance of stock cultures The ZR-75-1 human breast cancer cell line can be obtained from the American Type Culture Collection (Rockville, Md.). The cells are routinely cultured in phenol red-free RPMI 1640 medium supplemented with 10 nM $E_2$, 15 mM Hepes, 2 mM L-glutamine, 1 mM sodium pyruvate, 100 IU penicillin per ml, 100 ug streptomycin sulfate per ml, and 10% (v/v) fetal bovine serum (FBS), in a water-saturated atmosphere of 95% air: 5% $CO_2$ at 37° C.

Stock cultures in their logarithmic growth phase are harvested with 0.05% trypsin/0.02% EDTA (w/v) in Hanks' balanced salts solution and resuspended in $E_2$- and phenol red-free RPMI 1640 medium containing 5% (v/v) dextran-coated charcoal (DCC)-treated FBS and 500 ng of bovine insulin per ml, but otherwise supplemented as described above for maintenance of stock cultures. Cells were plated in 24-well Linbro culture plates (Flow Laboratories) at a final density of 0.5–4.0×10⁴ cells/well.

Fourty-eight hours after plating, fresh SD medium containing the appropriate concentrations of steroids are added. The final concentration of ethanol used for the addition of test substances does not exceed 0.12% (v/v) and has no significant effect on cell growth and morphology. The incubation media are replaced every other day and cells are harvested by trypsinization after 12 days of treatment, unless otherwise indicated. Cell number can be determined with a Coulter Counter.

Calculations and statistical analyses Apparent $IC_{50}$ values are calculated using an iterative least squares regression (Rodbard, Endocrinology 94: 1427–1437, 1974), while apparent inhibition constants (Ki values) are calculated according to Cheng and Prusoff (Biochem. Pharmacol. 22: 3099–3108, 1973).

% MPA (core loading)=0.28391+0.98720×[% Area ($\delta=0.65$ ppm)]

where % Area ($\delta=0.65$ ppm) is defined by:

% Area ($\delta=0.65$ ppm)=Area ($\delta=0.65$ ppm)/[Area ($\delta=5.20$ ppm)+Area ($\delta=0.65$ ppm].

Figure 3:
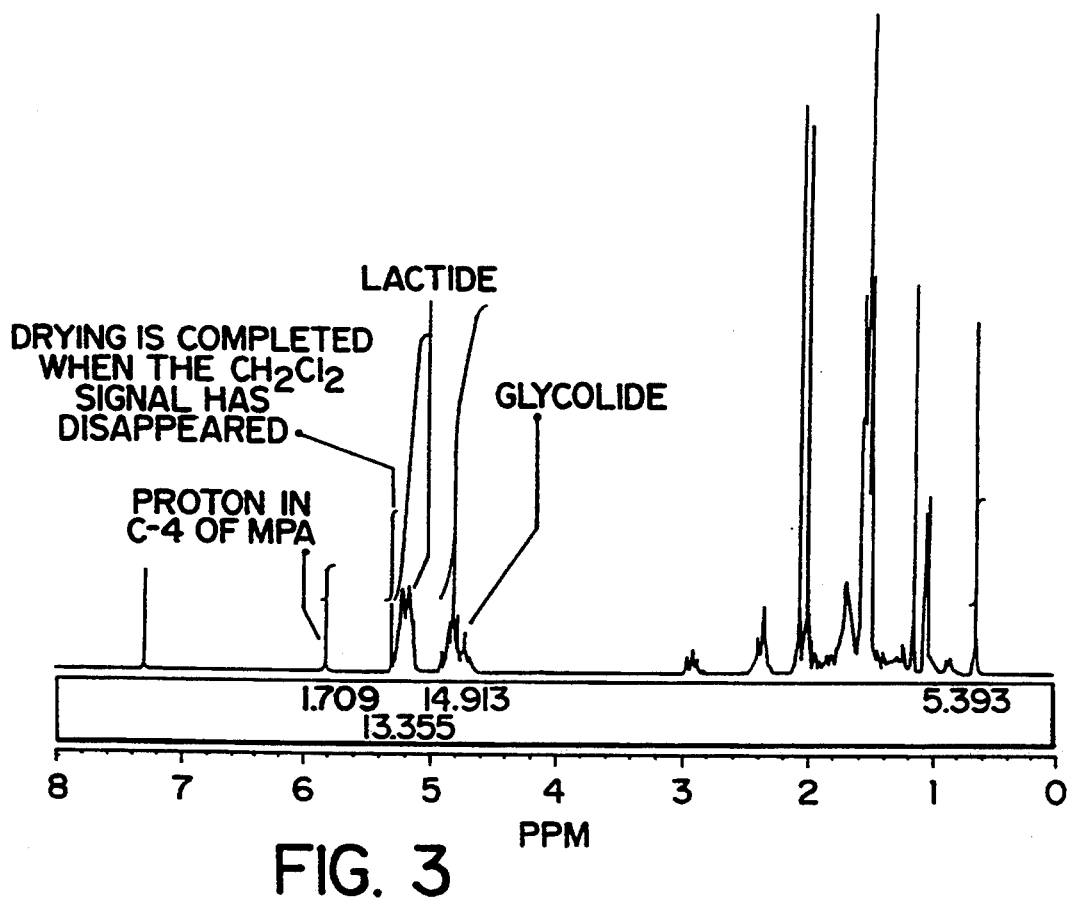
FIG. 3 is a Proton Nuclear Magnetic Resonance spectrum of $CDCl_3$— dissolved microparticles of the invention recorded on a Brucker AC-F300 FT NMR spectrometer. In the box, the area under the peaks at $\delta=0.65$ ppm for MPA and at $\delta=5.20$ ppm for lactide are used for core loading determination using the formula.
Figure 4:
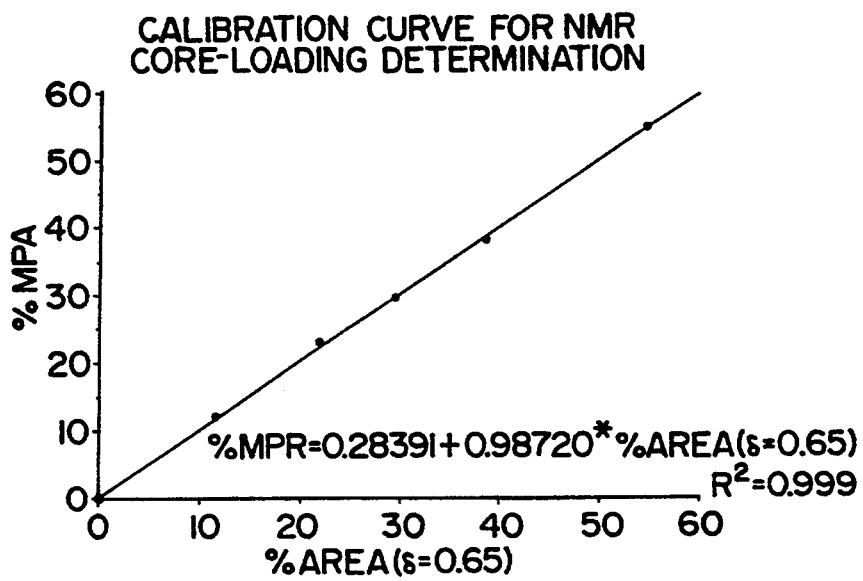

FIG. 4 is a standard curve for the determination of the core loading derived from NMR data as similar to that of FIG. 3 for known mixtures of polymer and MPA.

Figure 5:
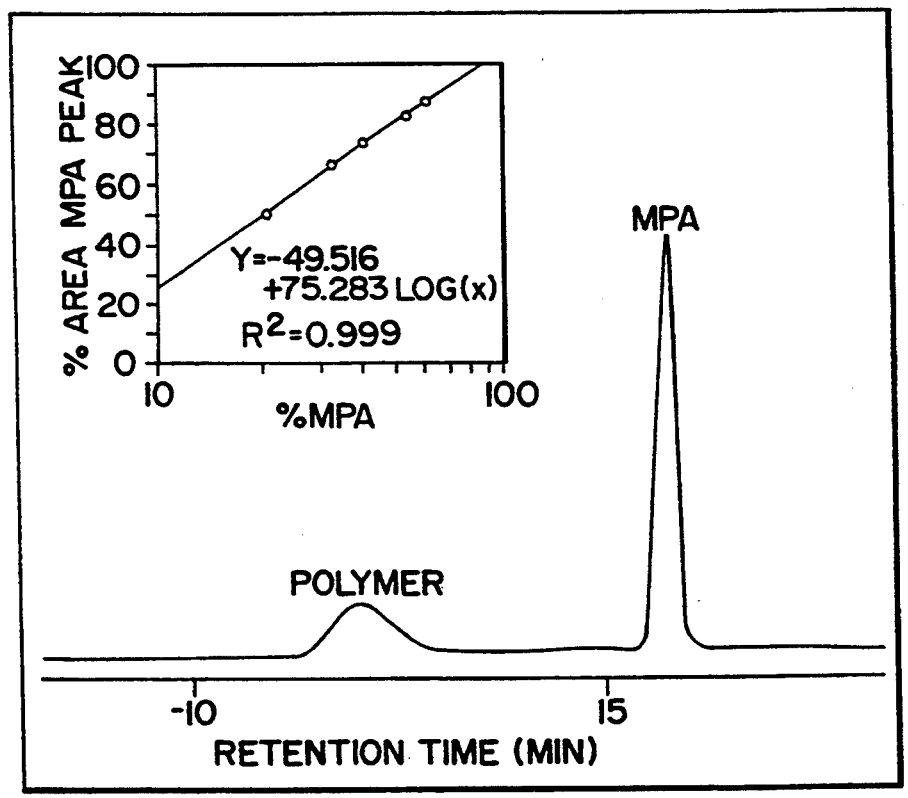

FIG. 5 is a chromatogram of sustained release MPA microspheres separated by steric exclusion chromatography (SEC) for core-loading determination. The peak at the retention time of 12 min corresponds to the polymeric sustained release binder while the peak at the retention time of 15.6 min is MPA. The insert of FIG. 5 is a calibration curve made from standard concentrations PLG/MPA mixtures. The area of the MPA peak is expressed versus the logarithm of the percentage of MPA in a known mixture with 50:50 poly [DL-lactide-co-glycolide].

Figure 6A:
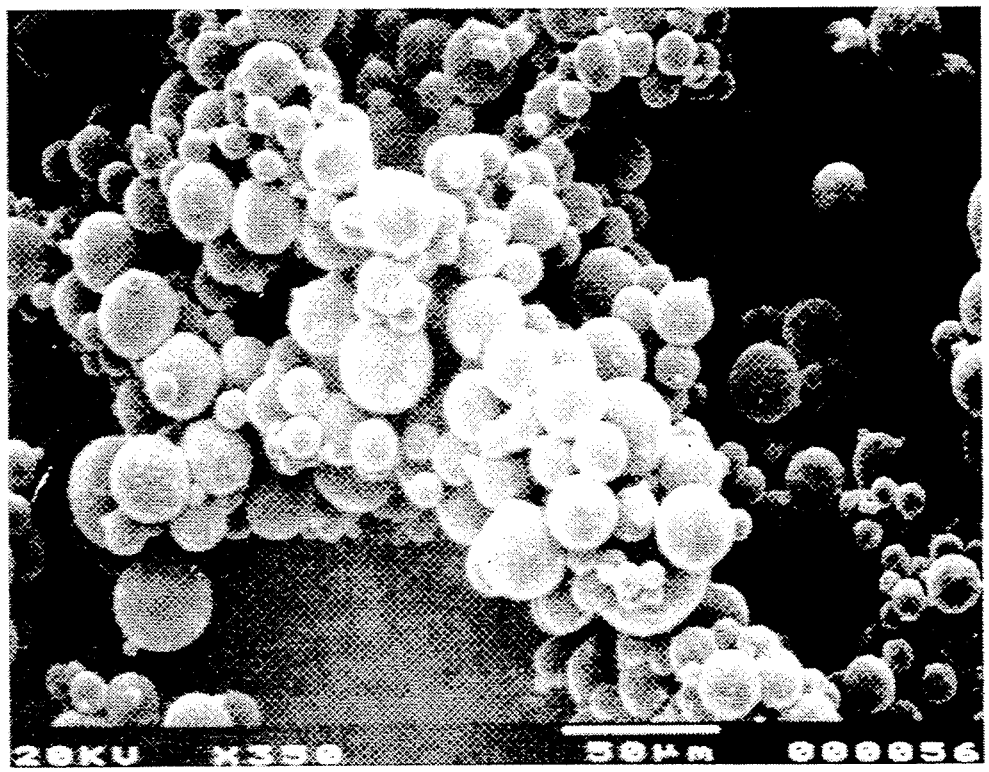
Figure 6B:
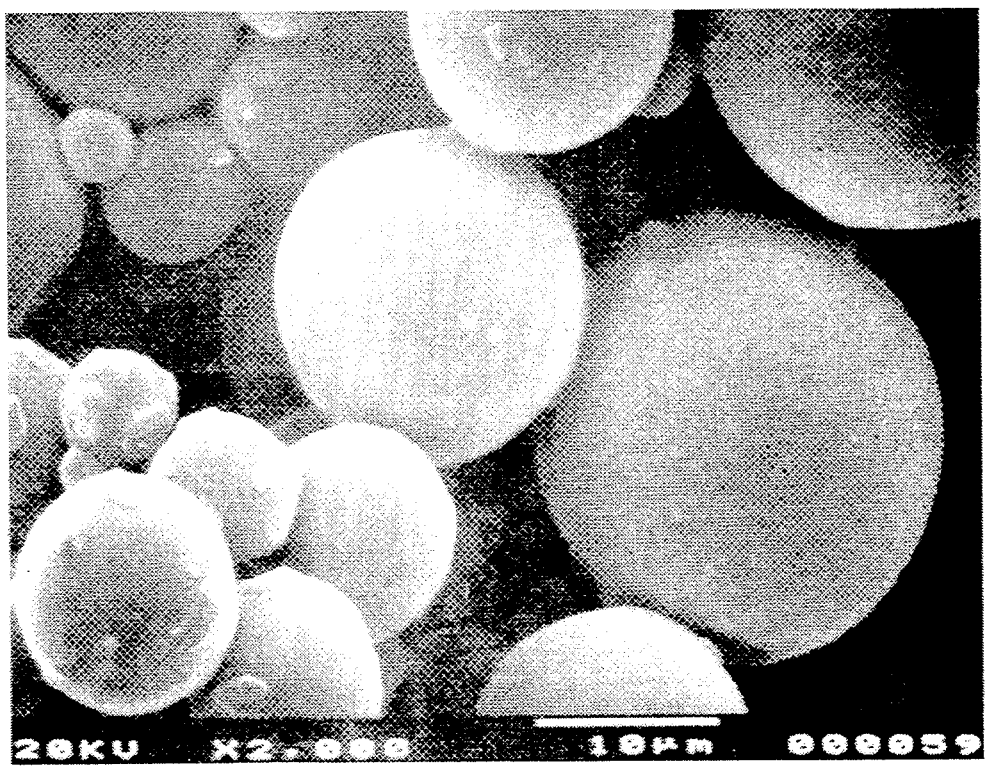

FIGS. 6A and 6B are scanning electron microscopy (SEM) photographs of MPA microspheres at (A) magnification of 350 and (B) magnification of 2000.

Figure 7A:
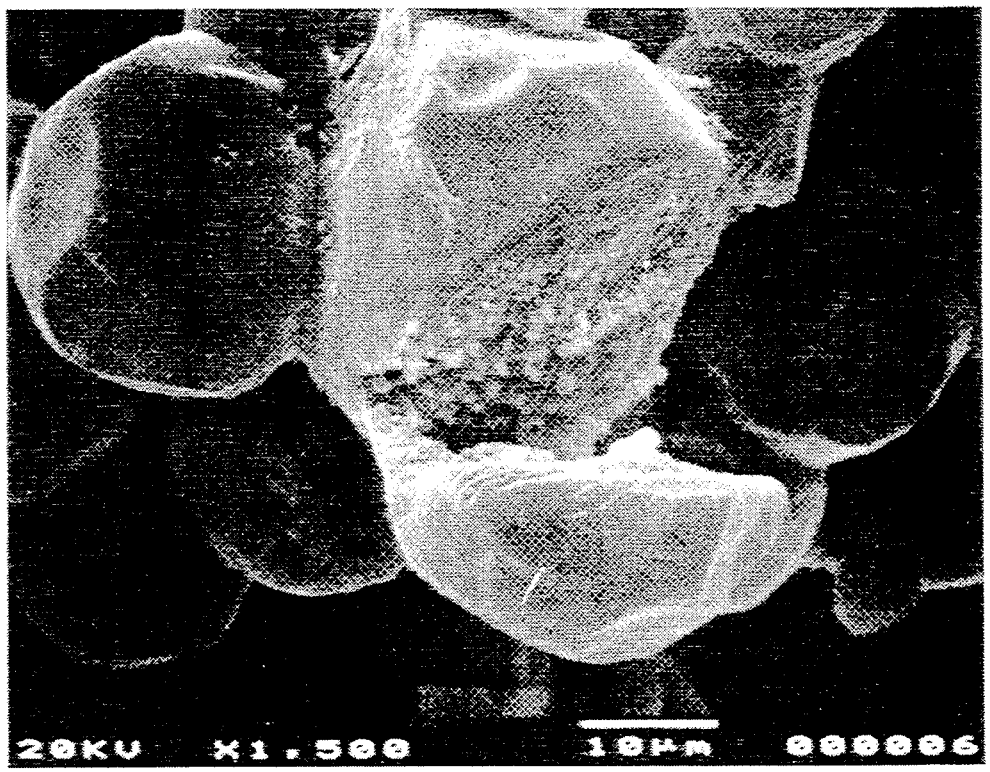
Figure 7B:
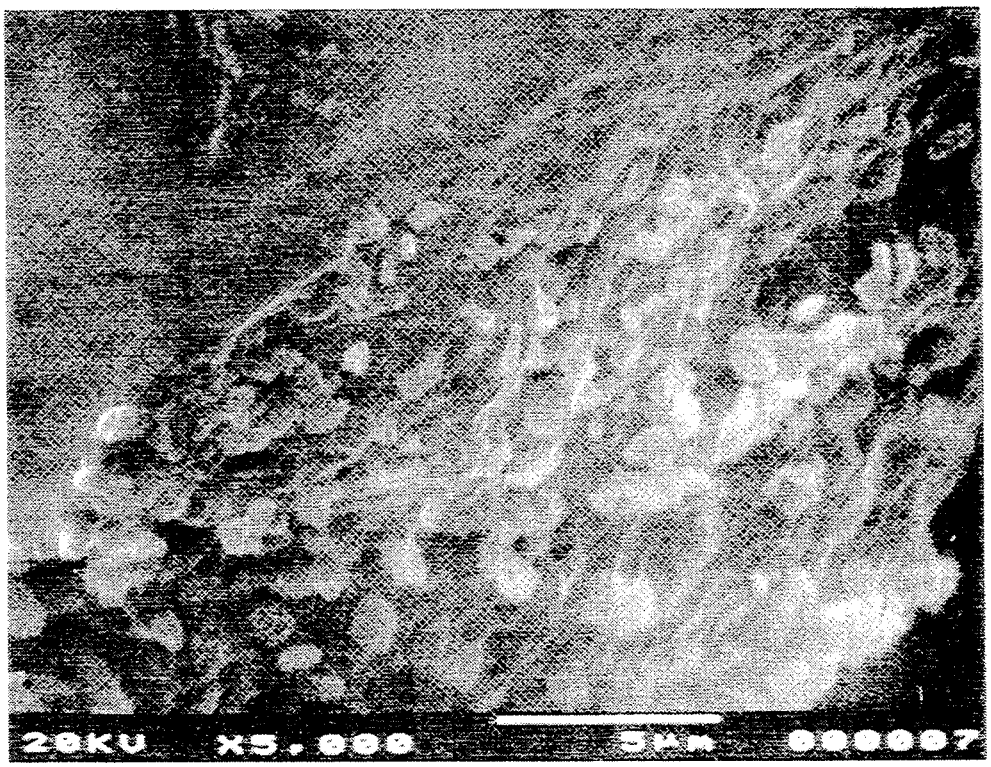

FIGS. 7A and 7B are scanning electron microscopy (SEM) photographs of a transverse section of MPA microspheres of the invention at (A) magnification of 1500 and (B) magnification of 5000.

Figure 8:

FIG. 8 shows the size distribution of MPA microspheres determined by scanning electron microscopy. The percentage of microspheres in each size range is expressed versus the size range ($\mu$m).

Figure 9:
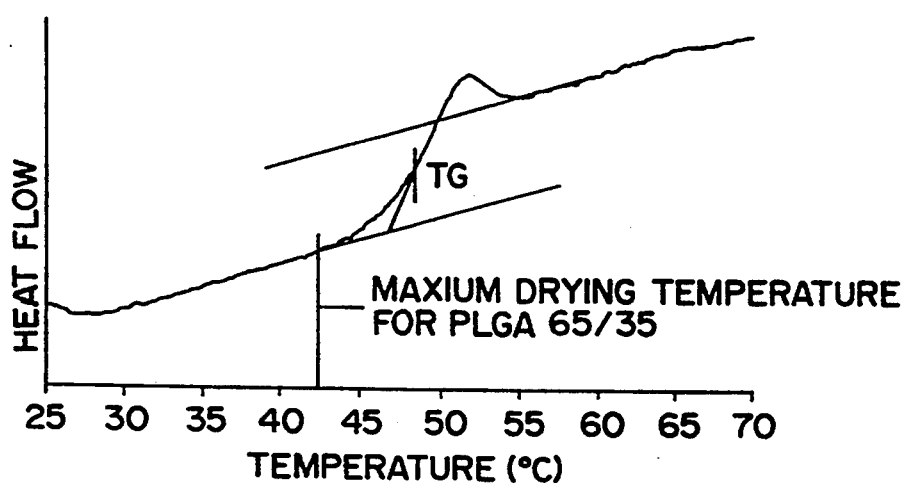

FIG. 9 is a differential scanning calorimetry (DSC) curve where the heat flow (difference of energy between the sample and the reference at defined temperature; the heat flow is directly proportional to the calorific capacity of the sample). This curve shows the glass transition temperature (Tg) of batch MPA encapsulated in 65:35 poly[DL-lactide-co-glycolide]microsphere of the invention with 33% loading of MPA.

Figure 10:
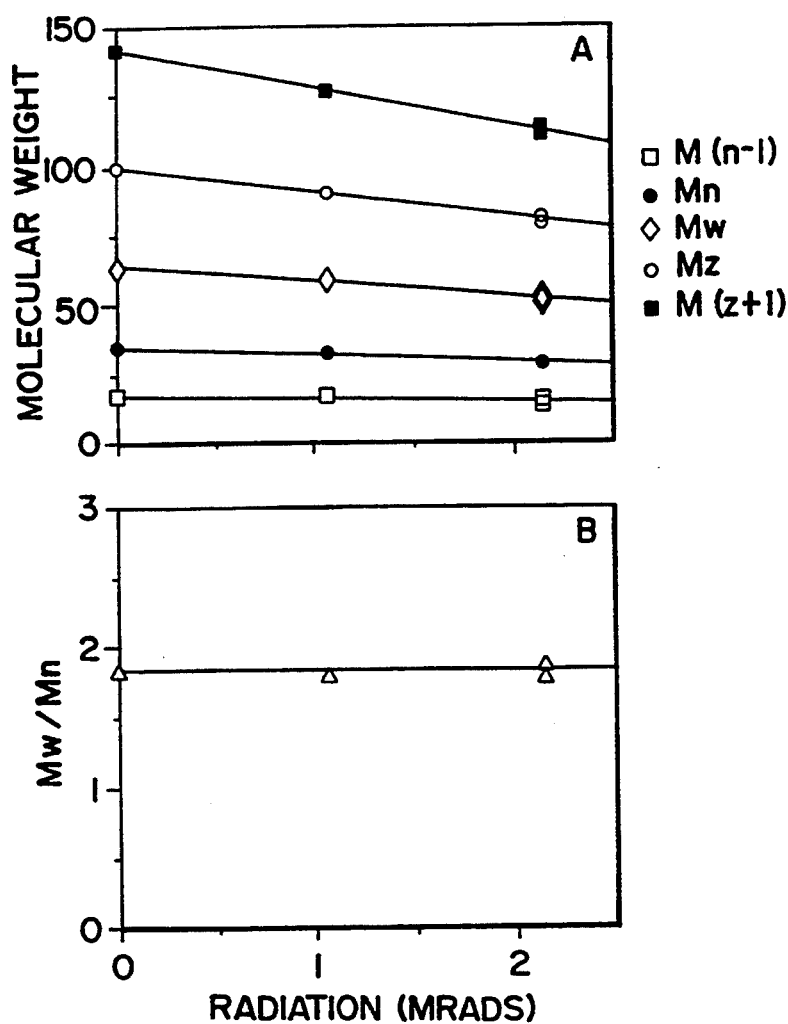

FIG. 10 shows, in (A), the variation of the different parameters [M(n−1), Mn, Mw, Mz,M(z+1)] characteristics of the molecular mass of 50:50 poly[DL-lactide-co-glycolide] following exposure to the indicated levels of gamma irradiation (Mrad); and, in (B), the variation of the polydensity (Mw/Mn) versus the level of gamma irradiation (Mrad).

Figure 11:
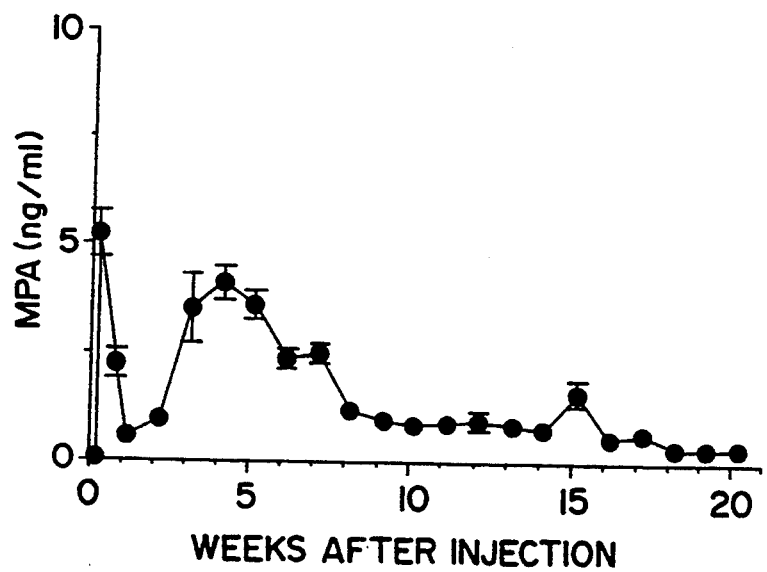

FIG. 11 shows the serum levels of MPA over time in New Zealand white rabbit following a single subcutaneous injection of 50 mg of MPA encapsulated in 50:50 poly[DL-lactide-co-glycolide]microspheres.

Figure 12:
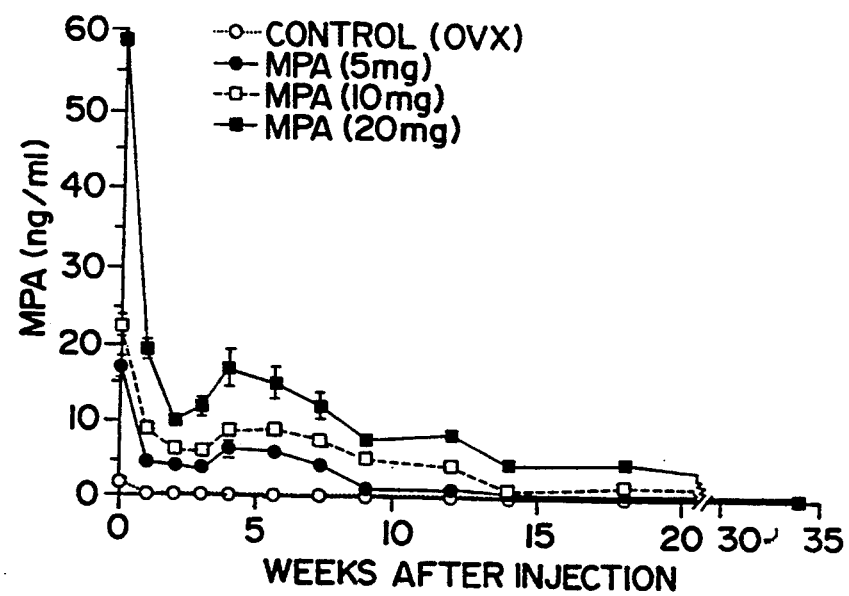

FIG. 12 illustrates the serum levels of MPA over time in ovariectomized female Sprague-Dawley rats after a single subcutaneous injection of the indicated amount of MPA encapsulated in 50:50 poly[DL-lactide-co-glycolide]microspheres (1 nM=0.386 ng/ml).

Figure 13:
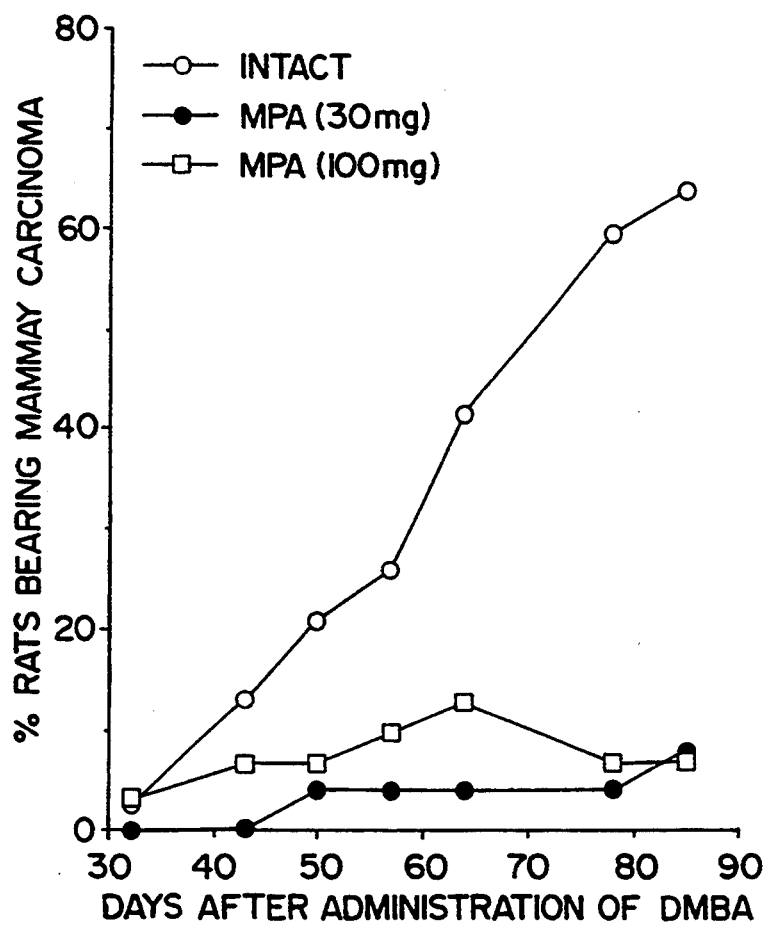

FIG. 13 is a graph showing the percent of rats bearing dimethylbenz(a)anthracene (DMBA)-induced mammary tumors as a function of time following single injection of MPA microspheres (30 and 100 mg of MPA or vehicle (control)) before administration of DMBA in the rat (1 nM=0.386 ng/ml).

A better understanding of the multiple endocrine activity of synthetic progestins is required not only for their more rational use in the prevention and therapy of breast and endometrial cancers as well as endometriosis and bone loss but also to avoid side effects caused by interaction with steroid receptors unnecessary for the desired beneficial effect.

Precise analysis of the biological actions of synthetic "progestins" having affinity for many steroidal receptors would ideally require the selection of in vitro models possessing functional receptors for all major classes of steroids. For this purpose, we have chosen the ZR-75-1 human breast cancer cell line, which possesses functional receptors for estrogens, androgens, progesterone and glucocorticoids (Vignon et al., J. Clin. Endocrinol. Metab. 56: 1124–1130, 1983) in order to compare the relative contribution of the different steroid receptor systems in the control of cell proliferation by synthetic progestins. While estrogens are strongly mitogenic in ZR-75-1 cells (Poulin and Labrie, Cancer Res. 46: 4933–4937, 1986) and specifically regulate the expression and/or the secretion of several proteins (Dickson and Lippman, Endocr. Rev. 8: 29–43, 1987), androgens (Poulin et al., Breast Cancer Res. Treatm. 12: 213–225, 1988), glucocorticoids (Hatton, A. C., Labrie, F., unpublished results) as well as progestins (Poulin et al., Breast Cancer Res. Treatm. 13: 161-172, 1989) inhibit their proliferation through specific interactions with their respective receptors.

Many progestins have been used in the treatment of breast cancer, including MPA (Blossey et al., Cancer 54: 1208-1215, 1984; Hortobayyi et al., Breast Cancer Res. Treatm. 5: 321-326, 1985), MGA (Johnson et al., Semin. Oncol. 13(Suppl.): 15-19, 1986; Tchekmedyan et al., Semin. Oncol. 13 (Suppl.): 20-25, 1986) and norethindrone (Clavel et al., Eur. J. Cancer Clin. Oncol. 18: 821-826, 1982; Earl et al., Clin. Oncol. 10: 103-109, 1984). Using the in vitro system of human breast cancer ZR-75-1 cells, it has now been determined that the synthetic progestins or anabolic steroids, Nor-testosterone, R1881, dromostanolone, fluoxymesterone, ethisterone, methandrostanolone, oxandrolone, danazol, stanozolol, calusterone, oxymetholone, cyproterone acetate, chlormadinone acetate and norgestrel, possess androgenic activity at low concentrations. In addition to inhibition of cell growth, the secretion of two glycoproteins, namely gross cystic disease fluid protein-15 (GCDFP-15) and GCDFP-24 is markedly stimulated by androgens (Simard et al., Mol. Endocrinol. 3: 694-702, 1989; Simard et al., Endocrinology 126: 3223-3231, 1990). Measurements of GCDFP-25 or GCDFP-24 secretion can thus be used as sensitive parameter or marker of androgen action in these cells. In fact, changes in GCDFP-15 and GCDFP-24 secretion are opposite to the changes in cell growth under all experimental conditions examined. All the synthetic progestins or anabolic steroids studied in connection with the invention exhibit androgenic activity on ZR-75-1 breast cancer growth and secretion of GCDFP-15 and GCDFP-24.

Identification of the receptors (estrogen, androgen, progesterone and glucocorticoid) responsible for the action of the compounds is essential in order to assess the potential actions (including adverse effects) of such compounds. It is thus especially important to assess the specific interaction at low concentrations with the androgen receptor since such low concentrations do not interact with the glucocorticoid receptor, thus avoiding or minimizing secondary side effects.

One method for inhibiting growth of breast and endometrial cells is activation of the androgen receptor with an effective compound having an affinity for the receptor site such that is binds to the androgen receptor at low concentrations while not significantly activating other classes of steroid receptors linked to potential side effects. It is important to select compounds having maximal affinity for the androgen receptor which have minimal or no virilizing effects in women. In order to minimize interaction of such compounds with the glucocorticoid and estrogen receptors, it is important to use low dose of the compounds. It is also important to choose steroids having androgenic activity at low concentrations which are not metabolized into estrogens under in vivo conditions which, at the low concentrations used, will not lead to significant activation of receptors other than the androgen receptors.

Compounds used in the invention, particularly anabolic steroids and synthetic progestins, vary markedly, over different concentrations, in their ability to activate different classes of steroidal receptors. By carefully controlling concentration, in accordance with the invention, it is possible to selectively cause activation of desired receptors while not causing significant activation of receptors whose activation is undesirable. For example, at the low concentrations specified herein, MPA can be utilized to desirably activate androgen receptors while substantially avoiding side effects associated with glucocorticoid activation which have plagued prior art treatments.

Thus, this invention provides a novel method for prevention and therapy of breast and endometrial cancer as well as other diseases responsive to activation of the androgen receptor, e.g. bone loss and endometriosis. In this invention, the amount of the androgenic compounds administered is much lower than previously used in art for the treatment of breast and endometrial cancer.

MONITORING BLOOD CONCENTRATION OF ANDROGENS OF THE INVENTION

To help in determining the potential effects of the treatment, blood concentrations of the compound can be measured. For example, measurements of plasma medroxyprogesterone acetate (MPA) levels can be made by radioimmunoassay following extraction as follows:

Antibody Preparation

Antibody 144 A was raised in rabbits against 17-hydroxyprogesterone-3-0-carboxymethyloxime-BSA. The labeled steroid used in the radioimmunoassay (RIA) was methyl-17α-hydroxyprogesterone acetate, 6α-[1,2-$^3$H(N)]- obtained from NEN (CAT NO: NET 480) while the reference preparation was medroxyprogresterone acetate (MPA) obtained from Steraloids. The assay buffer used was 0.1% gelatin in 0.1M sodium phosphate, 0.15M sodium chloride, 0.1% sodium azide, pH 7.2. The extraction solvent mixture was ethyl ether-acetone (9:1, v:v) [EEA] while the LH-20 chromatography solvent mixture was iso-octane: toluene: methanol (90:5:5;v:v:v) [IOTH].

Extraction Procedure

One ml of plasma was extracted twice with 5 ml of EEA. The extracts were evaporated to dryness with nitrogen and the remaining residue was dissolved in one ml of IOTH. The extracts were then subjected to LH-20 chromatography on 10×30 on columns (Corning CAT NO: 05 722 A) filled with 2 g of LH-20 (Pharmacia). The gel was washed with 30 ml of IOTH before addition of one ml of sample and elution with IOTH. The first 6 ml were discarded. The following 10, 16.5 and 27.5 ml of eluent were fraction I (progesterone), II (MPA) and III (17-LH-progesterone), respectively. Fraction II was evaporated to dryness and reconstituted in 1.5 ml of assay buffer.

Radioimmunoassay

To each 12×75 mm borosilicate test tube was added: 0.2 ml containing 25,000 DPM of tritiated steroid, 0.5 ml of reference preparation ranging from 5 to 5000 pg/tube or 0.5 ml of extracted sample fraction II, 0.2 ml of antiserum 144 A diluted 1/5000 or 0.2 ml of assay buffer to account for non specific binding. The tubes were then incubated overnight at 4° C. Then, 0.2 ml 2% charcoal Norit-A, 0.2% Dextran T-70 diluted in water was added. The tubes were then shaken gently and, after 10 min, they were centrifuged at 2000×g for 10 min. The supernatant was mixed with 8 ml of Formula-989 (NEN: NEF-989) and the radioactivity was counted in a β-counter.

The lower and upper limits of detection of MPA are 10 and 10000 pg/ml, respectively, while the slope (LOGIT-LOG) is -2.2 and the $ED_{50}$ value is 315 pg/ml. Non-specific and net binding are 1.5 and 45%, respectively. Antibody 144 A is highly specific for MPA since cross-reactivity with progesterone, 20α-OH-Prog, pregnenolone, 17-OH-pregnenolone, DHT, androstenedione, testosterone, 3α-diol, estrone, estradiol and cortisol is less than 0.1%.

Calculations and Statistics

RIA data were analyzed using a program based on model II of Roadbard and Lewald (In: 2nd Karolinska Symposium, Geneva, 1970, pp. 79–103). Plasma MPA levels are usually shown as the means ±SEM (standard error of the mean) of duplicate measurements of individual samples. Statistical significance is measured according to the multiple-range test of Duncan-Kramer (Kramer, C. Y., Biometrics 12: 307–310, 1956).

A Test Compound's Relative Effect On Various Receptors

To assist in determining the activity of the potential compounds on the various steroid receptors, androgen, glucocorticoid, progesterone and estrogen-receptor-mediated activities of synthetic progestins and anabolic steroids can be measured in ZR-75-1 human breast cancer cells using cell growth as well as GCDFP-15 and GCDFP-24 release as parameters of response (Poulin and Labrie, Cancer Res. 46: 4933–4937, 1986; Poulin et al., Breast Cancer Res. Treatm. 12: 213–225, 1988; Poulin et al., Breast Cancer Res. Treatm. 13: 161–172, 1989; Poulin et al., Breast Cancer Res. Treatm. 13: 265–276, 1989; Simard et al., Mol. Endocrinol. 3: 694–702, 1989; Simard et al., Endocrinology 126: 3223–3231, 1990).

The following properties permit measurement of progesterone receptor (PgR) activity:1) the addition of insulin completely reverses the inhibition due to the interaction of the progestin R5020 with the PgR in ZR-75-1 cells, and 2) the antiproliferative effect of R5020 is observed only under $E_1$-stimulated conditions. These two characteristics of ZR-75-1 cell growth permit study of the extent to which a tested compound's effects on ZR-75-1 cells are attributed to its interaction with PgR by evaluating the effect of insulin and/or estrogen addition on the growth response measured at the end of a 15-day incubation of ZR-75-1 cells with the test compounds.

The contribution of the estrogen receptor (ER), on the other hand, can be directly measured by incubating ZR-75-1 cells in the presence of absence of estrogen in the medium.

In order to analyze the interactions of synthetic progestins or anabolic steroids with the androgen receptor (AR) and glucocorticoid receptor (GR) in their inhibitory action on cell growth, one takes advantage of the additivity of the anti-proliferative effects of androgens and glucocorticoids in this cell line (Poulin et al., Breast Cancer Res. Treatm. 12: 213–225, 1988; Hatton and Labrie, F., unpublished data). Thus, one can saturate AR with 5α-dihydrotestosterone (DHT) and then measure the effect on cell proliferation resulting from the addition of a putative glucocorticoid. On the other hand, the effect of a putative androgen can similarly be measured following saturation of GR by dexamethasone (DEX). The specificity of the growth-inhibitory activity thus observed with the test compound can also be further assessed by its reversibility using the appropriate antagonist (i.e. antiglucocorticoid or antiandrogen). Thus, in the presence of excess androgen (1 μM DHT) in the presence of $E_2$ and insulin, glucocorticoid effects can be assessed with precision and with no interference by the other receptors. The same applies to study of the role of AR when the cells are incubated in the presence of excess glucocorticoid (3 μM DEX), in the presence of $E_2$ and insulin. As demonstrated by detailed kinetic studies, 1 μM DHT and 3 μM DEX exert maximal inhibitory effects on the AR and GR, respectively.

In addition, the possible antagonistic activities of "progestins" mediated through the AR and GR can be determined by saturating both receptor systems with DHT and DEX with one ligand being in far greater excess than the other in order to allow reversal through a single chosen receptor at a time. All experiments are performed with ZR-75-1 cells grown in $E_2$-supplemented media containing insulin in order to prevent the PgR-mediated effect of "progestins" on cell growth.

Using the foregoing techniques, I have found that numerous androgenic compounds which also activate other receptors (e.g. glucocorticoid or progesterone receptors) vary in their relative effects on different receptors as a function of concentration. By staying within concentration ranges defined herein, compounds of the invention may beneficially affect androgen receptors without substantial undesirable effects on other receptors.

Selection of Patients Who May Benefit from the Method's Described Herein

The appearance of breast cancer is usually detected by self breast examination and/or mammography. Endometrial cancer, on the other hand, is usually diagnosed by endometrial biopsy. Both cancers can be diagnosed and evaluated by standard physical methods well known to those skilled in the art, e.g. bone scan, chest X-Ray, skeletal survey, ultrasonography of the liver and liver scan (if needed), CAT scan, MRI and physical examination. Endometriosis can be diagnosed following pains or symptoms associated with menstruations in women while definitive diagnosis can be obtained by laparascopy and, sometimes, biopsy.

Bone density, on the other hand, can be measured by standard methods well known to those skilled in the art, e.g. QDR (Quantitative Digital Radiography), dual photon absorptiometry and computerized tomography. Plasma and urinary calcium and phosphate levels, plasma alkaline phosphatase, calcitonin and parathormone concentrations, as well as urinary hydroxyproline and calcium/creatinine ratios.

Breast or endometrial cancer, osteoporosis or otherwise insufficient bone mass, and other diseases treatable by activating androgen receptor may be treated in accordance with the present invention or prophylactically prevented in accordance herewith.

The methodology appropriate for assessing the contraceptive efficacy as well as the side effects can be found in Said et al., Contraception 37: 11–20, 1988.

Typically suitable androgenic compounds include 6-alpha-methyl,17-alpha-acetoxy progesterone or medroxyprogesterone acetate available, for example, from Upjohn and Farmitalia Carlo Erba, S.p.A. under the trade names Provera, DepoProvera or Farlutal, and the acronym MPA.

Other suitable androgenic compounds include those described in Labrie et al. (Fertil. Steril. 31: 29–34, 1979)

as well as anabolic steroids or progestins (Raynaud and Ojasso, In: Innovative Approaches in Drug Research, Elsevier Sci. Publishers, Amsterdam, pp. 47–72, 1986; Sandberg and Kirdoni, Pharmac. Ther. 36: 263–307, 1988; and Vincens, Simard and De Lignieres, Les Androgenes. In: Pharmacologie Clinique, Base de Thérapeutique, 2iéme Edition, Expansion Scientifique (Paris), pp. 2139–2158, 1988), as well as Calusterone (7β,17α-dimethyltestosterone), anabolic steroids (Lam, Am. J. Sports Medicine 12, 31–38, 1984; Hilf, R., Anabolic-androgenic steroids and experimental tumors. In: (Kochachian, C. D., eds.), Handbook of Experimental Pharmacology, vol. 43, Anabolic-Androgenic Steroids, Springer-Verlag, Berlin, 725 pp, 1976), fluoxymesterone (9α-fluoro-11β-hydroxy-17α-methyltestosterone), testosterone 17β-cypionate, 17α-methyltestosterone, Pantestone (testosterone undecanoate), $D^1$-testololactone and Andractim.

Other typical suitable androgenic compounds are cyproterone acetate (Androcur) available from Shering AG, 6-alpha-methyl, 17-alpha-acetoxy progesterone or medroxyprogesterone acetate (MPA) available from, among others, Upjohn and Farmitalia, Calbo ERba, Gestodene available from Shering, megestrol acetate (17α-acetoxy-6-methyl-pregna-4,6-diene-3,20-dione) available from Mead Johnson & Co., Evanswille, Ind., under the trade name of Megace. Other synthetic progestins include Levonorgestrel, Norgestimate, desogestrel, 3-ketodesogestrel, norethindrone, norethisterone, 13α-ethyl-17-hydroxy-18,19-dinor-17β-pregna-4,9,11-triene-20-yn-3-one (R2323, gestrinone), demegestone, norgestrienone, gastrinone and others described in Raynaud and Ojasso, J. Steroid Biochem. 25: 811–833, 1986; Raynaud et al., J. Steroid Biochem. 12: 143–157, 1980; Raynaud, Ojasoo and Labrie, Steroid Hormones, Agonists and Antagonists, In: Mechanisms of Steroid Action (G. P. Lewis and M. Ginsburg, eds), McMillan Press, London pp. 145–158 (1981). Any other progestin derivative having the above-described characteristics could also be useful for the invention.

The androgenic compound is preferably administered as a pharmaceutical composition via topical, parenteral or oral means. The compound can be administered parenterally, i.e. intramuscularly or subcutaneously by injection or infusion by nasal drops, by suppository, or where applicable intravaginally or transdermally using a gel, a patch or other suitable means. The androgenic compound may also be microencapsulated in or attached to a biocompatible, biodegradable polymer, e.g. poly(d,1-lactide-co-glycolide) and subcutaneously or intramuscularly injected by a technique called subcutaneous or intramuscular depot to provide continuous, slow release of the compound over a period of 30 days or longer. In addition to the oral route, a preferred route of administration of the compound is subcutaneous depot injection. DepoProvera can be released at a relatively constant rate for approximately 3 months after intramuscular administration of an aqueous dispersion.

The amount of each compound administered is determined by the attending clinician taking into consideration the patient's condition and age, the potency of each component and other factors. In the prevention of breast and endometrial cancer, as well as bone loss, according to this invention, the following dosage ranges are suitable.

The androgenic composition is preferably administered in a daily dosage which delivers less than 25 mg of active androgenic steroid per 50 kg of body weight.

A dosage of 1–10 mg per 50 kg of body weight, especially 3–7 mg (e.g. 5 mg) is preferred. The dosage selected preferably maintains serum concentration below 50 nanomoles per liter, preferably between 1.0 nanomoles per liter and 10, 15 or 25 nanomoles per liter depending on patient's response. The dosage needed to maintain these levels may vary from patient to patient. It is advisable for the attending clinician to monitor levels by the techniques described herein and optimize dosage accordingly. For prophylactic purposes, administration of the androgen is preferably started in the perimenopausal period for the prevention of breast and endometrial cancer and bone loss in normal women. The androgen may be associated with an accepted dose of an estrogen used to prevent other signs and symptoms of menopause. In women, when estrogen formation and/or action has been blocked for treatment of endometriosis, leiomyomata, breast cancer, uterine cancer, ovarian cancer or other estrogen-sensitive disease, administration of the androgen can be started at any time, preferably at the same time as blockade of estrogens.

The androgen for intramuscular or subcutaneous depot injection may be microencapsulated in a biocompatible, biodegradable polymer, e.g., poly(d,1-lactide-co-glycolide) by, among other techniques, a phase separation process or formed into a pellet or rod. The microspheres may then be suspended in a carrier to provide an injectable preparation or the depot may be injected in the form of a pellet or rod. See also European patent application EPA No. 58,481 published Aug. 25, 1982 for solid compositions for subdermal injection or implantation or liquid formulations for intramuscular or subcutaneous injections containing biocompatible, biodegradable polymers such as lactide-glycolide copolymer and active compounds. These formulations permit controlled release of the compound.

The androgens useful in the present invention can be typically formulated with conventional pharmaceutical excipients, e.g., spray dried lactose and magnesium stearate into tablets or capsules for oral administration.

The active substance can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol. Of course, taste-improving substances can be added in the case of oral administration forms.

As further forms, one can use plug capsules, e.g., of hard gelatin, as well as closed soft-gelatin capsules comprising a softener or plasticizer, e.g. glycerine. The plus capsules contain the active substance preferably in the form of granulate, e.g., in mixture with fillers, such as lactose, saccharose, mannitol, starches, such as potato starch or amylopectin, cellulose derivatives or highly dispersed silicic acids. In soft-gelatin capsules, the active substance is preferably dissolved or suspended in suitable liquids, such as vegetable oils or liquid polyethylene glycols.

In place of oral administration, the active compound may be administered parenterally. In such case, one can use a solution of the active substance, e.g., in sesame oil or olive oil. The active substance can be microencapsulated in or attached to a biocompatible, biodegradable polymer, e.g. poly(d,1-lactide-co-glycolide) and subcutaneously or intramuscularly injected by a technique called subcutaneous or intramuscular depot to provide continuous slow release of the compound(s) for a period of 2 weeks or longer.

The invention also includes kits or single packages containing the pharmaceutical composition, active ingredients, or means for administering the same for use in the prevention and treatment of breast and endometrial cancer as well as bone loss and treatment of endometriosis as discussed above. The kits or packages may also contain instructions on how to use the pharmaceutical compositions in accordance with the present invention.

Following the above therapy using the described regimen, tumor growth of breast and endometrial cancer as well as bone loss and endometriosis can be relieved while minimizing adverse side effects. The use of the described regimen can also prevent appearance of the same diseases.

When controlled release formulations are desired, controlled release binders suitable for use in accordance with the invention include any biocompatible controlled-release material which is inert to the active ingredient and which is capable of incorporating the active ingredient. Numerous such materials are known in the art. Preferred controlled-release binders are materials which are metabolized slowly under physiological conditions following their subcutaneous or intramuscular injection in mammals (i.e. in the presence of bodily fluids which exist there). The binder may be one whose rate of biodegradation is sufficiently slow that pure microspheres of binder (i.e. without steroid or other active ingredient) having an average diameter above 20 microns would not be completely biodegraded for at least one month following subcutaneous or intramuscular injection. Appropriate binders include but are not limited to biocompatible polymers and copolymers previously used in the art in sustained release formulations. Such biocompatible compounds are non-toxic and inert to surrounding tissues following subcutaneous or intramuscular injection and do not trigger significant adverse effects such as immune response, inflammation, or the like. They are metabolized into metabolic products which are also biocompatible and easily eliminated from the body.

For example, a polymeric matrix derived from copolymeric and homopolymeric polyesters having hydrolysable ester linkages may be used. A number of these are known in the art to be biodegradable and to lead to degradation products having no or low toxicity. Typically, such preferred polymers are polyglycolic acids (PGA) and polylactic acids (PLA), poly(DL-lactic acid-co-glycolic acid)(DL PLGA), poly(D-lactic acid-co-glycolic acid)(D PLGA) and poly(L-lactic acid-co-glycolic acid)(L PLGA). The preferred ratio for lactic acid and glycolic acid polymers in poly(lactic acid-co-glycolic acid) is in the range of 100:0 (i.e. pure polylactide) to 50:50. Other useful biodegradable or bioerodable polymers include but are not limited to such polymers as poly(ε-caprolactone), poly(ε-caprolactone-CO-lactic acid), poly(ε-caprolactone-CO-glycolic acid), poly(β-hydroxy butyric acid), poly(alkyl-2-cyanoacrilate), hydrogels such as poly(hydroxyethyl methacrylate), polyamides, poly(amino acids) (i.e. L-leucine, glutamic acid, L-aspartic acid and the like), poly (ester urea), poly (2-hydroxyethyl DL-aspartamide), polyacetal polymers, polyorthoesters, polycarbonate, polymaleamides, polysaccharides and copolymers thereof. Numerous appropriate materials are commercially available, for example, polylactic acid-co-glycolide (available from Birmingham Polymer Inc, Birmingham Ala. or from Dupont Company, Washington D.C.).

Sustained release particles of the invention have a rate of release of active ingredient calculated to provide substantially constant serum concentrations. When a low dose androgen is provided in accordance with the invention, androgen is released by the binder at a rate maintaining serum levels of said androgen between 1 and 50 nanomoles per liter, typically between 1 and 25, preferably between 1 and 15, and most preferably between 1 and 10 nanomoles per liter; when administered under standard conditions discussed below. Standard conditions are defined (only for the limited purpose of measuring the inherent rate-of-release property of sustained release particles discussed herein) as percutaneous injection of 10 mg of particles (in the form of 20 mg of a pharmaceutical composition having a 1:1 ratio (w:w) of particles to 2% of aqueous carboxymethyl cellulose carrier (w/w)) to the back of young female Sprague-Dawley rats. Serum concentration of the androgen is then measured by taking periodic serum samples from the rats beginning 48 hours after administration and ending 28 days after administration to assure that serum levels are being maintained within the desired range throughout the period.

The rate of release of sustained release particles may be varied by varying any of a number of parameters (or a combination of parameters) known in the art to alter release rate. These parameters include but are not limited to composition of sustained release binder, particle size and core loading. For example, it is known that a polylactide binder is hydrolyzed more slowly and hence (other factors being equal) releases active ingredient more slowly than copolymers of lactic acid and glycolic acid. For such copolymers, rate of release increases with increasing mole percent glycolide. For equal weights of particles, rate of release increases with decreasing particle size because a larger total surface area (sum of all particles) is presented by smaller particles. Likewise, increasing the core loading (percent of active compound in particles) increases the rate of release. These parameters may also be varied in known ways to control duration of release. A detailed discussion of the preparation of sustained release pharmaceuticals is provided by F. Lim (F. Lim, Biomedical Application of Microencapsulation, Franklin Lim, ed., CRC Press, Boca Ration, 1984), the entire disclosure of which is incorporated by reference as though fully set forth herein.

The standard conditions and measurements set forth above relate only to the inherent rate-of-release property of the particles and are only definitional. Particles having the appropriate rate-of-release may, as discussed in detail herein, be formulated and administered in a variety of ways. They are put to a variety of uses, and administered in a broad dosage range (see below). The particles may provide sustained release of active ingredient for as little as 28 days, or for substantially longer periods, for example two months, three months, six months or longer. In other words, while the particles must maintain appropriate blood levels for 28 days, they are desirably formulated to maintain those blood levels for considerably longer.

Dosage may be varied by the attending clinician to maintain serum levels at the desired level, for example between 1 and 50 nanomoles of androgen per liter. Human dosage necessary to achieve circulating serum levels similar to those achieved in the rat under standard conditions tend to be about 30 times the rat dosage although this will vary with the metabolism of individual patients. Thus, sustained release MPA particles, for example, which maintain 30 nanomolar serum concentrations following 10 mg injections in the rat under standard conditions would be expected to provide approximately 30 nanomolar concentration in humans following a 300 mg injection, 20 nanomolar concentration following a 200 mg injection, 15 nanomolar concentration following a 150 mg injection, etc . . . The foregoing dosages are by weight of the sustained release particles and do not include carrier. Dosages of the final pharmaceutical composition must be adjusted to account for carrier. For example, where a 100 mg dosage of particles is desired, a composition which has a 1:1 particle to carrier ratio should be administered at a dosage of 200 mg. Likewise dosage should be adjusted based on the release rate of the sustained release particles under standard conditions. To achieve the same serum concentration level, for example, particles with a release rate of 5 nanomolar (under standard conditions) would be administered at about twice the dosage of particles with a release rate of 10 nanomolar (under standard conditions).

Typically, the attending clinician will begin with a dose calculated to maintain serum levels of active ingredient between 1 and 10 nanomolar, e.g. from 3–7 nanomolar. Depending upon patient response, dosage may subsequently be raised or lowered. It is preferred that short duration particles (e.g. about 28 days) be used until optimum dosage is determined. Thereafter, longer term sustained release particles may be administered at a dosage for maintaining optimum blood levels. The dosage is of course adjusted as described above for any difference in standard release rates between the shorter and longer duration particles.

Preferred active compounds include all of the androgenic compounds discussed herein, for example, medroxyprogesterone acetate (6-alpha-methyl,17-alpha-acetoxy progesterone) or "MPA", which can be obtained, among other sources, from Upjohn and Farmitalia Carlo Erba, S.p.A., under the trade name Provera, Depoprovera or Farlutal; and megestrol acetate (17α-acetoxy-6-methyl-pregna-4,6-diene-3,20-dione) or "MGA", which can be obtained among other sources, from Mead Johnson & Co., under the trade name of Megace.

It is preferred that the sustained release particles be substantially spherical. This may be accomplished, for example, by dissolving active ingredient and sustained release binder in organic solvent and then introducing the solvent into water together with stirring. Small microspheres of binder having active ingredient dispersed therein are thereby formed due to the lack of solubility of the microspheres in water by adding to an excess of water. The microspheres are freed of a significant amount of the organic solvent so long as the organic solvent is miscible in water. A surfactant may be added to aid separation of microspheres from solvent during microsphere formation in water-average microsphere size may be increased by less vigorous stirring or decreased by more vigorous stirring. For purposes of easy injectability, when administered to patients, and also for facilitating subsequent removal of undesirable residual organic solvent, smaller microspheres are preferred. Typically, average microspheres size is between 5 and 40 $\mu$m and preferably between 9 and 28 $\mu$m.

In one preferred embodiment, the encapsulation of MPA is accomplished by forming an aqueous suspension of microdroplets containing a mixture of MPA and polymer in methylene chloride. Polymer may be, for example, a 50:50 copolymer of lactic and glycolic acid. The formation of microspheres is controlled by a surfactant such as poly(vinyl alcohol). The droplets are hardened by removal of methylene chloride extracted with a large amount of water, a technique which gives a better shape for droplets than the usual vacuum evaporation process of the microspheres. The size of the microsphere is controlled by the amount of surfactant and the speed of stirring of the suspension mixture.

The overall distribution of particle sizes may vary, but a narrow and more uniform range is preferred. Preferably, at least 90% of the particles are between 1 and 40 $\mu$m. Most preferably, at least 90% are between 9 and 28 $\mu$m. As used herein, size of microspheres refers to the diameter of individual microspheres, even if undesirably agglomerated to other microspheres. Size of irregular particles refers to the longest straight line between any two parts of the particle. Size may be measured by viewing a representative sample of particles under an electron microscope.

Representative organic solvents for use in preparing microspheres include but are not limited to methylene chloride, ethyl acetate, acetone, diethyl ether, tetrahydrofuran, hexafluoroacetone, hexafluoroisopropanol, acetonitrile and mixtures of the solvents. Representative surfactants used in the first part of the fabrication of microspheres by solvent extraction microencapsulation process, as described in Example 3, include but are not limited to poly(vinyl)alcohol), polyvinyl pyrrolidone, carboxymethylcellulose, gelatin, starch, talc, magnesium sulfate, calcium carbonate and ionic agents. The surfactant is preferably added in an amount between about 1 and 10 percent of water (v/v).

While the ratio of water to solvent (including dissolved binder) may vary, large excesses of water (e.g. a water to solvent ratio of 5 and 20 (v/v) or above) is preferred.

The binder is preferably added to organic solvent at a concentration between about 1 percent and about 20 percent (v/v) depending upon solubility. Preferably, the amount of solvent is near the minimum necessary to fully dissolve binder and active ingredient. When dissolution is incomplete, additional solvent may be added. The ratio of active ingredient to binder is determined by the desired core loading which preferably varies between 1:4 and 7:3 (w/w) and more preferably between 3:7 and 3:2). The degree of core loading may be selected in order to influence rate-of-release of the sustained release product or duration of release, or other parameters known in the art.

In the fabrication of microspheres using a solvent-extraction microencapsulation process as described in example 3, the preferred solvent for dissolution of medroxyprogesterone acetate and the polymer or copolymer is methylene chloride, but other solvents partially miscible with water and possessing a low degree of human toxicity are also suitable (e.g. ethyl acetate, acetone, diethyl ether, tetrahydrofuran, hexafluoroacetone, hexafluoroisopropanol, acetonitrile and mixtures of these solvents). Moreover, toxicity of solvent is not a significant factor when solvent is substantially removed using the solvent removal techniques described herein. The preferred surfactant is poly(vinyl alcohol) but other surfactants are also suitable: polymeric dispersing agents (i.e. poly(vinyl pyrrolidone) carboxymethylcellulose, gelatin, starch), talc, magnesium sulfate, calcium carbonate and ionic agents.

Microparticles may also be formed using a casting process, wherein a solution of MPA and polymer or copolymer in a appropriate solvent (e.g. one of the solvents discussed above) is cast. The solvent is then evaporated at atmospheric pressure. The film thus obtained is heated and extruded through a mesh wire. The resulting rods or fragments are ground into microparticles. Microparticles may be divided into size ranges with an appropriate molecular sieve. Average size is typically from 1 to 250 $\mu$m, preferably 5–100 $\mu$m, and more preferably from 9 to 28 $\mu$m. Solvent removal and ease of injection are both facilitated by using smaller particles, preferably where average size (and 90% of particles) are less than 40 $\mu$m.

In accordance with the present invention, the preferred pharmaceutical composition has a core loading in the range of 20 to 70% MPA or MGA, more particularly between 30 and 60%. Active ingredient to binder ratio is preferably 1:4 to 7:3, for example 3:7–3:2.

Information about the methods of general use for the preparation of controlled release formulations of other compounds can be found in Kitchell and Wise, In Methods in Enzymology, Academic Press, vol. 112, pp. 436–448; Beck and Tice, In Long Acting Steroid Contraception (D. R. Mishell Jr., ed), Raven Press: New York, pp. 175–199, 1983 and Wise et al., In Biology and Medicine (G. Gregotiadis, ed), Academic Press: New York, pp. 237–270, 1979, the entire disclosure, of which are hereby incorporated by reference as though fully set forth herein.

The steroid is preferably administered in a daily dosage which delivers less than 25 mg of active MPA or MGA per 50 kg of body weight, preferably 1–10 mg, most preferably 3–7 mg (e.g. 5 mg). The dosage selected preferably maintains serum concentrations below 50 nanomoles per liter, preferably between 1.0 nanomoles per liter and 10, 15 or 25 nanomoles per liter, depending on the patient's response.

In accordance with the present invention, one parenteral injection preferably contains less than 2.0 grams of active ingredient (e.g. medroxyprogesterone acetate or megestrol acetate), more preferably between 0.15 and 1.0 grams.

It is highly desirable to remove as much residual organic solvent as possible from the sustained release particles. Indeed, some organic solvents are so toxic that they cannot be used in the formation of sustained release particles unless a means for their effective removal exists. "Unincorporated" organic solvent which is not trapped within the physical structure of the particle, e.g. is merely in contact with the surface, can be easily removed by conventional techniques (e.g. multiple washings with water, air stream, etc . . . ). Organic solvent incorporated within the physical structure is more problematic, and a novel method of solvent removal is discussed below.

Solvent removal is facilitated by preparing particles of low particle size. Preferably, the particles have an average size of less than 40 microns, e.g. between 5 and 40 microns, more preferably between 9 and 28 microns. Most preferably, size distribution is such that 90% of the particles are within the above-stated size ranges.

In preferred embodiments, following formation of particles, unincorporated solvent is removed by conventional techniques such as multiple aqueous washings and/or air drying.

Removal of solvent than preferably proceeds by subjecting the particles to a mild vacuum wherein pressure is not less than 50 torr and temperature is not greater than the lesser of (A) 30° C. and (B) 7° C. below the glass transition temperature of the particles.

The particles are substantially freed of residual solvent, including solvent physically incorporated within the particle by subjecting the particles to a strong vacuum (less than 1.0 torr and preferably less than 0.5 torr) at a temperature between 7° and 20° C. less than the glass transition temperature (Tg°) of the particles, preferably between 7° and 15° C., below Tg, and more preferably between 7° and 12° C. below Tg. This strong vacuum step is continued for a time period sufficient to reduce residual organic solvent in the particles to a concentration of less than 0.1% (by weight relative to total weight of said particles). Preferably, residual solvent is reduced to less than 0.05%, and more preferably less than 0.02%.

Glass transition temperature may be measured or calculated in a number of ways known in the art, including but not limited to measuring and graphing heat flow versus temperature by standard techniques as illustrated in FIG. 9. Maximum heating temperature should preferably be set no higher than the end of the linear portion of the curve below the glass transition temperature (also as illustrated in FIG. 9). Higher temperatures can undesirably cause agglomeration of particles or formation of thermal degradation products. By maintaining temperature in the range of the present invention, particles are substantially free flowing and free of thermal degradation products. However, the use of moderate heat in accordance with the invention substantially aids removal of organic solvent.

In preferred embodiments, a mild vacuum-step or other method or reducing residual solvent to less than 5%, and preferably less than 2 percent (by weight relative to total weight of particles) preceeds the strong vacuum step. Higher solvent levels can undesirably cause particle rupture during the strong subsequent vacuum step. Such rupture can have undesirable effects on a particles rate-of-release characteristics.

When the foregoing mild vacuum step is used, typical time periods are from 1 to 10 days, preferably 1 to 5 days and more preferably from 2 to 4 days. Typical time periods for the strong vacuum step are from 1 to 20 days, preferably 2 to 15 days, and more preferably from 3 to 10 days. However, duration of the strong vacuum step should continue until residual organic solvent is reduced to below the desired level. The level of residual solvent may be determined by known methods, for example, as illustrated in Example 6 below. The method of the invention has successfully been used to reduce solvent to less than 0.02% (w/w), the lowest detectable amoung using GC analysis as in Example 6.

Sustained release particles prepared in accordance with the invention may be prepared for final use in a variety of known ways. Preferably, they are sterilized by known techniques (e.g. as described in Example 10). They may then be combined with pharmaceutically acceptable diluents or carriers. Known preservatives may also be added.

Preferably, the concentration of sustained release particles (by weight relative to total weight of the composition) is between about 10 and 70 percent. The carrier is preferably one in which the binder of the particles is substantially insoluble, e.g. carboxymethycellulose in water, distilled water or saline.

In accordance with the present invention the preferred microspheres are characterised by the absence of thermal decomposition impurities. This is achieved by using low temperature and high vacuum for drying the microspheres.

The preferred carrier for parenteral injection of the microparticles in accordance with the present invention is selected from the group consisting of saline, aqueous diluted solution of carboxymethylcellulose, aqueous diluted solution of glycerin, aqueous diluted solution of glycol, water or aqueous diluted ethanol. More particularly, the preferred carrier is a 2 to 5% aqueous solution of carboxymethylcellulose.

Preferred methods for administering the sustained release formulations of the invention include but are not limited to subcutaneous or intramuscular injection and oral administration.

Because of the low dosages used in accordance with the invention, side effects are sufficiently reduced that prophylactic use of the methods of the invention is much more practicable and more likely to gain widespread acceptance than are higher dose methods. Because treatment dosage is already low, efficacy of "preventive therapy" need not be jeopardized by using a lesser dosage.

EXAMPLE 1

Prevention of Mammary Carcinoma Induced by Dimethylbenz(a)-anthracene (DMBA) in the Rat, By Low Dose Medroxyprogesterone Acetete ("MPA")

Figure 1:
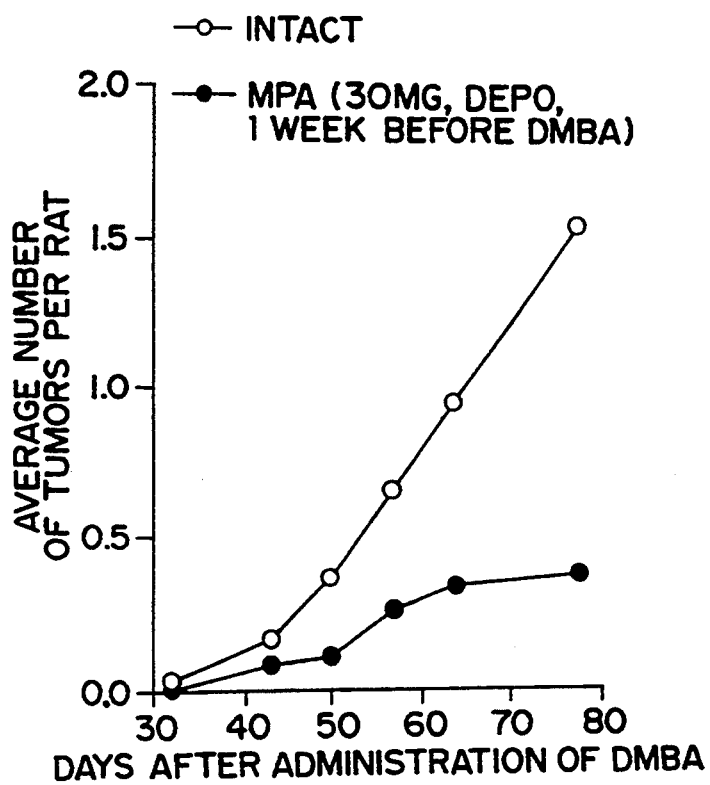
FIG. 1 is a comparative graph over time of the number of tumors observed in a group of rats protected by a method in accordance with the invention, i.e. administration of 30 mg of DepoProvera 1 week before tumors were induced by administration of dimethylbenz(a)anthracene (DMBA) versus an unprotected control group.

To illustrate the efficacy of the present invention in reducing the incidence of mammary carcinoma, FIG. 1 illustrates the effect of a single subcutaneous injection of Depo-Provera (Medroxyprogesterone Acetate (MPA) (30 mg)) one week before inducing carcinoma with dimethylbenz(a)anthracene. FIG. 1 shows the period from 30 to 85 days following administration of DMBA. One curve in FIG. 1 shows the average number of tumors per animal in the group protected by Depo-Provera while the other curve shows the average number of tumors per animal in the unprotected group. It is estimated that the 30 mg. injection of Depo-Provera would release approximately 0.17 mg. of active medroxyprogesterone acetate per day over a six-month period. As may be seen by comparing the two graphs in FIG. 1, the Depo-Provera-treated group showed much greater resistance to the development of tumors than did the unprotected group. After 85 days an average of 1.89 tumors per rat was observed in the unprotected group, while only 0.30 tumor per rat was observed in the Depo-Provera protected group. Tumor number and size measured with calipers were determined weekly.

EXAMPLE 2

Figure 2:
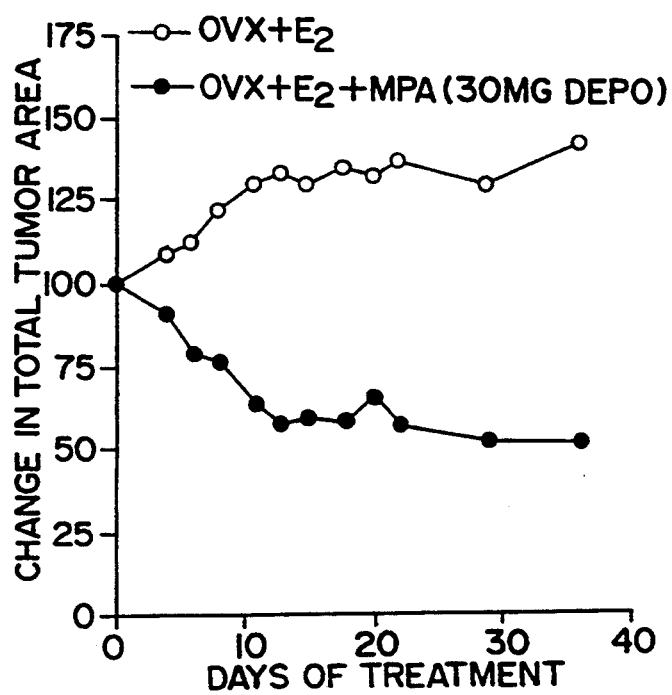
FIG. 2 is a comparative graph over time of estradiol-stimulated growth of tumors in ovariectomized rats (●—●) versus untreated control group (○—○). Tumors were induced using dimethylbenz(a)anthracene. Estradiol was used to stimulate growth of tumors in both treatment and control group rats. Each animal in the treatment group received a single subcutaneous administration of 30 mg of DepoProvera. Results are expressed in percentage of change in total tumor area in each group.

Treatment of Mammary Carcinoma Induced By Dimethylbenz(a)-anthracene In the Rat, By Low Dose Medroxyprogesterone Acetate FIG. 2 illustrates the inhibition of mammary carcinoma growth which may be achieved in accordance with the methods of the invention. Tumors were induced in ovariectomized rats using dimethylbenz(a)anthracene. Estradiol was used to stimulate growth in both a treatment and control group of rats. Each animal in the treatment group received a single subcutaneous administration of 30 mg of Depo-Provera (which is estimated to release approximately 0.17 mg. per day of active medroxyprogesterone acetate for a period of about six months). This figure illustrates the average estradiol-stimulated change in total tumor area in each group following treatment. As may be seen in FIG. 2, the group treated with Depo-Provera exhibited significantly less tumor growth than the untreated group.

EXAMPLE 3

Preparation of Medroxyprogesterone Acetate-containing Microspheres by the Solvent Extraction Process Complete dissolution of the polymeric material 50/50 poly(DL-lactide-co-glycolide) (supplied by Birmingham Polymer Inc. Birmingham, Al.) ("PLG") is achieved by overnight shaking with solvent using a KS-10 shaker (from BEA Enprotech Corp.) set at a speed of 150-200 rev/min. The solvent used is methylene chloride ($CH_2Cl_2$), obtained from BDH and distilled once immediately before use. The polymer (1.50 g) is added to the glass bottle already containing $CH_2Cl_2$ (15.00 g) under continuous shaking. Medroxyprogesterone acetate (0.75 g) is then added with continuous shaking to form a PLG-MPA-$CH_2Cl_2$ solution.

Separately, in a 250-ml resin kettle (from Kontes) 94 ml of water and 6 ml of a surfactant [poly(vinylalcohol) (PVA) (Airvol TM 205, supplied by Air Products & Chemicals)] are mixed and maintained under continuous stirring with a teflon turbine-like impeller set on a laboratory heavy-duty stirrer. Then, 1.16 ml of methylene chloride is added to the surfactant solution for saturating the aqueous solution and avoid the extraction of methylene chloride at this stage, using a 2.0 ml glass pipet inserted through one of four ports in the upper-part of the resin-kettle. Stirring is then continued for 5 min. at 850 rpm. Microspheres are then prepared by adding the previously-prepared PLG-MPA-$CH_2Cl_2$ solution into the stirring $CH_2Cl_2$-saturated PVA solution using an all-polypropylene syringe equipped with a 16 gauge 6-inch long needle. After adding the MPA solution, stirring is continued for a further period of 5 min.

Hardening of Microspheres

The hardening step is performed as follows:
1) The content of the resin-kettle is rapidly poured into the a hardening bath and the resin-kettle is rinsed with distilled water and the contents once more poured into the hardening bath. The hardening bath consists of a large stainless steel beaker (7 l) containing 5 l of distilled water. Stirring is maintained at high speed (850 rpm) during 20 min. with a laboratory heavy duty stirrer equipped with a 2.5 inche, SS impeller.
2) The microspheres are then separated from the washing medium using a Millipore 142 mm filtration system. After hardening, the content of the bath is transferred to the 20 l Millipore dispensing pressure vessel. At that time, care must be taken in order to insure thorough rinsing of the hardening SS beaker in order to efficiently recover microspheres which settle down upon interruption of stirring. Microspheres are then collected on the 142 mm membrane (8 μm pore size) by pushing the content of the dispensing vessel through the membrane unit with compressed air (10 psi).

3) The membrane is then washed with distilled water and the microspheres are at the same time washed off the membrane down into a second hardening bath which is identical to the first one. Collection of microspheres on a 142 mm membrane is then performed for a second time as described above.

4) Final washing and drying of the microspheres are then performed in the Millipore 142 mm filtration system. A first drying step is achieved with a stream of air maintained at 10 psi, for 1 h. The microspheres are then transferred from the membrane to a desiccator containing −1 inch of Drierite and placed under moderate vacuum (70 torr) for a period of 2–3 days. Final drying is then achieved in a vacuum oven at 35°–40° C. and a pressure of 0.4 torr until solvent becomes undetectable by gas chromatography which has a limit of detection of $CH_2Cl_2$ of 0.02% (by weight relative to total weight of the microparticles). Hence, the technique removed substantially all of the residual organic solvent, and less than 0.02% remained.

EXAMPLE 4

Preparation of 60% Medroxyprogesterone Acetate (MPA)/40% Medisorb TM 85:15 DL Poly(Lactic-Co-Glycolic) Acid (PLGA) Microparticles by the Casting Method Medroxyprogesterone acetate (MPA) was used as obtained from Steraloids. Prior to use, the component had been characterized by UV spectroscopy and its melting point. Medisorb TM 85:15 DL poly(lactic-co-glycolic) acid had been obtained from DuPont and was also used as obtained. Methylene chloride (highest grade available) was obtained from Fisher Scientific. The polymer (6.0022 g) was dissolved in 24 ml of methylene chloride as a 25% (0.25 g PLGA/ml methylene chloride) solution. Medroxyprogesterone acetate (9.0022 g) was added to the polymer solution and stirring was continued to insure complete mixing. The solution was then cast on a clean, level glass plate using a Boston-Bradley adjustable blade to spread to a uniform thickness. The cast film was allowed to dry in a fume hood for several hours. After evaporation of most of the solvent, the resulting film was scraped from the glass plate and vacuum-dried at room temperature for four days.

The film formed in the casting step was of very low density since the solvent removal step left a very large void volume. The void volume was reduced to decrease permeation of fluids into the microparticles by a compression step, utilizing heat and hydraulic pressure. The film was extruded into rods with a Pasadena Hydraulics Inc. Press at about 125° C.

The extruded rods were ground into small particles using a commercial grinder with a cooled grinding chamber. Following grinding, the powder was passed through a series of U.S. Standard sieves to collect the microparticles in the size ranges of 38 to 125 μm, 125 to 180 μm, and 180 to 250 μm. The sieved microparticles were collected.

EXAMPLE 5

RESIDUAL SOLVENT EVAPORATION a) An Abderhalden apparatus (supplied by Aldrich Chemicals Co.) was used for drying. The most important feature of this glassware is that it allows simultaneous use of high vacuum and heating combined with the possibility of storing the sample for drying in the presence of a drying agent (molecular sieve 3A). In our study, high vacuum ($-10^{-2}$ torr) is achieved with a E2M5 Edwards vacuum pump. Heating of the sample for drying is achieved by refluxing a mixture of solvent: $CH_2Cl_2+$ Acetone in case of batch MPA-MB-V in order to obtain a temperature of 45° C.

b) Batches MPA-MB-VII to MPA-MB-XI, MPA-MFI-73, MPA-MLV-31, MPA-MLV-32, MPA-MLV-34, MPA-MLV-35, MPA-MLV-39 and MPA-MLV-40 were dried as follows: in all these batches, a vacuum oven was used to achieve further drying of the microspheres. Vacuum (0.4 torr) is achieved with a E2M5 Edwards vacuum pump. The temperature was well controlled (44° to 46° C.) and all these batches were dried at the same time in the system.

EXAMPLE 6

Determination of Residual Methylene Chloride

The residual methylene chloride concentration in microspheres is determined by GC analysis using a Varian 3700 Gas Chromatograph equipped with a DB-1 capillary column and a FID detector. The temperature program is 7 min at 40° C. before heating at the rate of 10° C./min until 200° C. (1 min) is reached. The injection volumes are 1.0 μl. For the purpose of GC analysis, microspheres (-25 mg) are dissolved in $CHCl_3$ (HPLC grade), 1 ml, then diluted with 5 ml iso-octane. The precise concentration of methylene chloride is determined using a calibration curve established from five standards. These standards are prepared from pure methylene chloride ($CH_2Cl_2$) and chloroform ($CHCl_3$) in concentrations ranging from 0.1 to 1.0% (w/w).

The following table shows results obtained for residual methylene chloride analysis:

| MPA system | % $CH_2Cl_2$ (w/w) |
|---|---|
| Casting process: batch: as prepared in Example 4. | 0.3 |
| Microsphere 50:50 DL-PLG | <0.02 |

EXAMPLE 7

MPA Core-loading Determination a) Nuclear magnetic resonance: This determination was made by NMR spectroscopy by analysis of the area under the peak of the 19-methyl group of MPA at $\delta=0.65$ ppm and the peak of hydrogen atoms of the polymer (multiplet at $\delta=5.20$ and at $\delta=4.8$). A Bruker AC-F 300 FT NMR spectrometer was used. See FIG. 3 for an example of NMR spectrum, and FIG. 4 an example of standard curves for this determination which are derived from NMR spectra of known mixtures of MPA and polymer.

b) Steric exclusion chromatography: The MPA core-loading measurement by steric exclusion chromatography (SEC) was made using a Perkin-Elmer 250 ISO/LC-30 SEC system with PLgel 50 Å 5 μm column and a PLgel mixed column using HPLC grade chloroform as eluant. For example, in FIG. 5, measurements of 50:50 PLG microspheres were carried out at 40° C.

and MPA and DL-PLG were well separated under these conditions. The core-loading of a sample was determined by measurement of the area under the MPA peak with reference to a calibration curve made from standard concentrations of PLG/MPA mixtures (insert).

EXAMPLE 8

Physical Characteristics of Microspheres Determined by Scanning Electron Microscopy (SEM)

In order to analyze their surface morphology, the microspheres were examined by electron scanning microscopy (SEM), using a JEOL JSM T330A apparatus. Samples were prepared by depositing microspheres on a double-face tape before spotting with a gold layer having a thickness of 500–600 A. These analyses have also been used to determine the mean diameter ($\phi$) of the microspheres. Those determinations are performed by manual counting and measuring all microspheres seen on the picture taken at low magnification (350×) (FIG. 6A). Larger magnification, up to 2000×, permits more detailed analysis of the surface of the microspheres (FIG. 6B).

For example, precise determination of the size distribution of MPA microspheres of batch MPA-MB-V was made by direct measurement of the diameter of the microspheres from the SEM photographs. As can be seen in FIG. 8, more than 95% of the 680 microspheres thus counted have a size smaller than 40 $\mu$m with an average diameter of 18.6±9.7 (S.D.) $\mu$m. Such a small size of microspheres facilitates the injection of the material and shortens the duration of release.

Transverse cut of a microspheres in FIG. 7 shows that MPA is concentrated in islets dispersed in the polymer.

EXAMPLE 9

Characterization of Microspheres by Differential Scanning Calorimetry (DSC)

Thermal analysis of samples was performed with a Perkin-Elmer DSC-7. The apparatus was calibrated with indium and operated at a scan speed of 10° C./min.

In FIG. 9, the DSC curve of MPA microspheres shows that the maximum drying temperature could be easily determined.

EXAMPLE 10

Sterilization of Microsphers

Before injection, the microspheres were sterilized by exposure to 2.2 Megarads of gamma radiation achieved with a Cobalt-60 source (Gammacell 200). The stability of MPA was checked by steric exclusion chromatography (SEC) while the stability of the polymer was analyzed by SEC using polystyrene standards for calibration and by the modification of the relative viscosity using a Ubbelohde capillary viscometer.

Exposure to gamma radiation (2.2 Megarads) does not damage MPA but the reduced specific viscosity of the microspheres in $CH_2Cl_2$ solution is loweredcd from 0.301±0.008 to 0.262±0.003 dL/g, thus indicating that some polymer chains have been broken.

Samples of batch MPA-MB-V have been exposed to different amounts of gamma radiation (0,1.1,2,2 Megarads) and the molecular mass distribution parameters [M(n−1), Mn, Mw, Mz, M(z+1)] (see FIG. 10A) as well as their polydispersity (Mw/Mn) (FIG. 10B) were measured.

These data indicate that the dominant process is a random scission of the polymer chains. Thus, the irradiated microspheres will be biodegradated more rapidly than unirradiated microspheres, and the effects of irradiation should be taken into account when microspheres are prepared, e.g. by setting the pre-irradiation rate-of-release slightly lower than desired for the final product.

EXAMPLE 11

Serum MPA Levels in Rabbits Injected Subcutaneously with MPA-Containing Microspheres New Zealand white rabbits (about 2.7 kg) were housed 1 per cage under a regimen of 10 h of light and 14 h of darkness (lights on at 07:00h) and received 16% "Tablets for rabbits+ obtained from Moulées Kiloplus (Québec, Canada) and tap water ad libitum. 50 mg of MPA-containing microspheres (batch MPA-MB-V) in suspension in a solution of 2% carboxymethylcellulose and 1% Tween 80 were in injected subcutaneously to a group of 10 rabbits. Blood samples were taken at different time intervals and the MPA concentrations were measured by RIA. Serum levels of MPA are reported in FIG. 11.

EXAMPLE 12

Serum MPA Levels in Rats Injected Subcutaneously with MPA-containing Microspheres of the Invention Young female Sprague-Dawley rats [Crl: CD(SD)Br] were obtained from Charles River Canada Inc. (St-Constant, Quebec) and housed 2 per cage under a regimen of 14 h of light and 10 h of darkness (lights on at 05:00 h). Animals received rat chow and tap water ad libitum.

Increasing doses (5,10 and 20 mg) of MPA-containing microspheres in suspension in a solution of 2% carboxymethylcellulose and 1% Tween-80 were injected subcutaneously to a group of 10 female rats (Sprague-Dawley). Blood samples were then taken at different time intervals and the MPA concentrations were measured by RIA. The results are shown in FIG. 12.

EXAMPLE 13

Prevention of Mammary Carcinoma Induced by Dimethylbenz(a)-anthracene (DMBA) in the Rat by Low Dose MPA (Microspheres).

MATERIALS AND METHODS

Animals and Induction of Mammary Carcinoma:

Mammary carcinoma was induced in female Sprague-Dawley (Crl: CD(SD)Br) rats (obtained from Charles River Canada Inc., St. Constant, Quebec) at 50 to 52 days of age by a single intragastric administration of 20 mg of dimethylbenz(a)anthracene (DMBA) (Sigma Chemicals co., St. Louis, Mo.) in 1 ml of corn oil.

Treatment

One week before administration of DMBA, animals were divided into 3 groups (intact, intact +30 mg MPA and intact +100 mg MPA) and received single s.c. administration of 30 mg or 100 mg MPA containing microspheres, respectively.

RESULTS

As illustrated in FIG. 13, 85 days after administration of DMBA, in intact animals, 63% of the animals had detectable mammary tumors while in animals pretreated with 30 mg of MPA (microspheres), only 7.4% and 6.3% of the animals had detectable mammary tumors, respectively. The present data clearly indicate that pretreatment with MPA microspheres inhibits the development of mammary carcinoma induced by DMBA in the rat, thus suggesting the possible use of MPA microcapsules for prevention of human breast cancer in women.

The terms and descriptions used herein are preferred embodiments set forth by way of illustration only and are not intended as limitations on the many variations which those skilled in the art will recognize to be possible in practicing the present invention as defined by the patent claims.

What is claimed is:

1. A method of treating or preventing breast cancer by administering to a patient in need of such treatment or prevention, a therapeutically effective amount of sustained release particles, with or without additional pharmaceutical carriers or diluents, said particles comprising an androgenic steroid dispersed within a sustained-release binder which is biocompatible with human tissue and which undergoes biodegradation in the body into biocompatible metabolic products, wherein said particles are capable, under standard conditions, of releasing said androgenic steroid during and as a result of said biodegradation of said binder at a rate and duration which maintains circulating serum levels of said androgenic steroid between 1.0 and 50.0 nanomoles per liter during a time period beginning 48 hours after administration and ending at least 28 days after administration, wherein said androgenic steroid has a Ki value of less than about $2 \times 10^{-8}$M for the androgen receptor, and an androgen receptor-mediated inhibitory effect on the growth of human breast cancer ZR-75-1 cells which reaches half-maximal value at a concentration below 3.0 nanomoles per liter, and no visible masculinizing activity.

2. The method of claim 1 wherein said binder is a polymeric matrix comprising copolymeric or homopolymeric polyesters having hydrolyzable ester linkages.

3. The method of claim 1 wherein said binder is a polylactide.

4. The method of claim 1 wherein said binder is a copolymer of lactide and at least one monomer selected from the group consisting of glycolide and caprolactone.

5. The method of claim 4 wherein said copolymer is between 50 and 90 mol-% lactide.

6. The method of claim 1 wherein the ratio of said androgenic steroid to said binder is between 1:4 and 7:3 (by weight).

7. The method of claim 1 wherein said binder is selected from the group consisting of poly($\epsilon$-caprolactone), poly($\epsilon$-caprolactone-CO-lactide acid), poly($\epsilon$-caprolactone-CO-glycolide), poly($\beta$-hydroxy butyrate), poly(alkyl-2-cyanoacrilate), hydrogels such as poly(hydroxyethyl methacrylate), polyamides, poly(amino acides) (i.e. L-leucine, glutamic acid, L-aspartic acid and the like), poly (ester urea), poly (2-hydroxyethyl DL-aspartamide), polyacetal polymers, polyorthoesters, polycarbonate, polymaleamides, polysaccharides and copolymers thereof.

8. The method of claim 1 wherein said particles are substantially free of thermal degradation impurities.

9. The method of claim 1 wherein the average particle size is between 5 and 40 μm.

10. The method of claim 1 wherein the average particle size is between 9 and 28 μm.

11. The pharmaceutical composition of claim 1 wherein said particles are microspheres having an average diameter between 5 and 40 μm.

12. The method of claim 1 wherein said particles are microspheres formed by dissolving said binder and said androgenic steroid into an organic solvent to form a solution, and then pouring said solution into water with sufficient stirring to form said microspheres and to assure that said microspheres have an average diameter between 5 and 40 μm.

13. The method of claim 1 wherein said androgenic steroid is medroxyprogesterone acetate.

14. The method of claim 1 wherein said androgenic steroid is megestrol acetate.

15. The method of claim 1 wherein at least 90% of said particles are less than 40 microns in size.

16. The method of claim 1 wherein at least 90% of said particles are between 9 and 28 microns in size.

* * * * *